United States Patent
Collins et al.

(10) Patent No.: US 11,112,763 B1
(45) Date of Patent: Sep. 7, 2021

(54) MONITORING AND PERFORMANCE MANAGEMENT SYSTEM FOR A NETWORK OF SMART FILTERING CONTAINERS

(71) Applicant: LARQ, Inc., Foster City, CA (US)

(72) Inventors: Doug Collins, Foster City, CA (US); Josh Abell, Foster City, CA (US); Li Zhang, San Ramon, CA (US); Justin Wang, Foster City, CA (US); Antonio Kaleb, Zagreb (HR)

(73) Assignee: LARQ, INC., Foster City, CA (US)

(*) Notice: Subject to any disclaimer, the term of this patent is extended or adjusted under 35 U.S.C. 154(b) by 0 days.

(21) Appl. No.: 17/102,307

(22) Filed: Nov. 23, 2020

Related U.S. Application Data

(63) Continuation-in-part of application No. 16/996,818, filed on Aug. 18, 2020.

(51) Int. Cl.
   *G05B 19/042* (2006.01)
   *G06Q 30/06* (2012.01)
   (Continued)

(52) U.S. Cl.
   CPC ....... *G05B 19/042* (2013.01); *B01D 35/1435* (2013.01); *C02F 1/003* (2013.01);
   (Continued)

(58) Field of Classification Search
   None
   See application file for complete search history.

(56) References Cited

U.S. PATENT DOCUMENTS

| 7,107,838 B2 | 9/2006 | Chai et al. |
|---|---|---|
| 7,487,677 B2 | 2/2009 | Chai et al. |

(Continued)

FOREIGN PATENT DOCUMENTS

| CN | 100574842 | 12/2009 |
|---|---|---|
| CN | 101795976 | 2/2013 |

(Continued)

OTHER PUBLICATIONS

App Store Preview, "PUR Faucet Mount Water Filter", last updated Mar. 20, 2018, retrieved on Feb. 14, 2021 from https://apps.apple.com/us/app/pur-faucet-mount-water-filter/id958274779.

(Continued)

*Primary Examiner* — Richard C Gurtowski
(74) *Attorney, Agent, or Firm* — ARC IP Law, PC; Joseph J. Mayo

(57) ABSTRACT

System that monitors and manages a network of smart filtering containers, such as water pitchers with integrated sensors. Measurements are collected from the containers and forwarded to a centralized system, such as an Internet server; data may be analyzed to determine performance modifications or recommendations for selected containers. Centralizing the data enables discovery of patterns and correlations across containers; for example, abnormal measurements from multiple pitchers in an area may suggest contamination of the area's water supply. The centralized system may automatically update settings of containers to optimize their performance. It may send messages to users suggesting different usage patterns or configurations. It may automatically order components such as replacement filters or upgrades. A water testing capability may also be provided; users may be sent water test strips that can be imaged using an associated mobile device app, and results may be forwarded to the central database for analysis.

30 Claims, 22 Drawing Sheets

(51) Int. Cl.
*C02F 1/00* (2006.01)
*C02F 1/32* (2006.01)
*B01D 35/143* (2006.01)

(52) U.S. Cl.
CPC ............... *C02F 1/008* (2013.01); *C02F 1/32* (2013.01); *G06Q 30/0633* (2013.01); *B01D 2201/52* (2013.01); *B01D 2201/54* (2013.01); *B01D 2201/56* (2013.01); *C02F 2209/008* (2013.01); *C02F 2209/40* (2013.01); *C02F 2303/04* (2013.01); *G05B 2219/2642* (2013.01)

(56) References Cited

U.S. PATENT DOCUMENTS

| | | |
|---|---|---|
| 7,666,288 B2 | 2/2010 | Sato |
| 7,905,144 B2 | 3/2011 | Thobe |
| 8,171,802 B2 | 5/2012 | Henderson et al. |
| 1,059,373 A1 | 3/2020 | Choi et al. |
| 2005/0229700 A1 | 10/2005 | Chai et al. |
| 2006/0060512 A1* | 3/2006 | Astle ............... B01D 29/606 210/85 |
| 2010/0133200 A1* | 6/2010 | Gin ..................... G01N 33/569 210/742 |
| 2010/0154534 A1* | 6/2010 | Hampton ............ G01F 23/265 73/304 C |
| 2010/0187168 A1 | 7/2010 | Moretto |
| 2016/0368802 A1* | 12/2016 | Yagita ..................... C02F 1/008 |

FOREIGN PATENT DOCUMENTS

| | | |
|---|---|---|
| CN | 206809883 | 12/2017 |
| CN | 207085689 | 3/2018 |
| CN | 109665639 | 4/2019 |
| WO | 2015/197725 A1 | 12/2015 |

OTHER PUBLICATIONS

AMAZON.com, "PUR PFM800HX Faucet Water Filtration System with Bluetooth Horizontal, Chrome", retrieved on Feb. 14, 2021 from https://www.amazon.com/PUR-PFM800HX-Horizontal-Bluetooth-MineralClear/dp/B01M0I5RII.

* cited by examiner

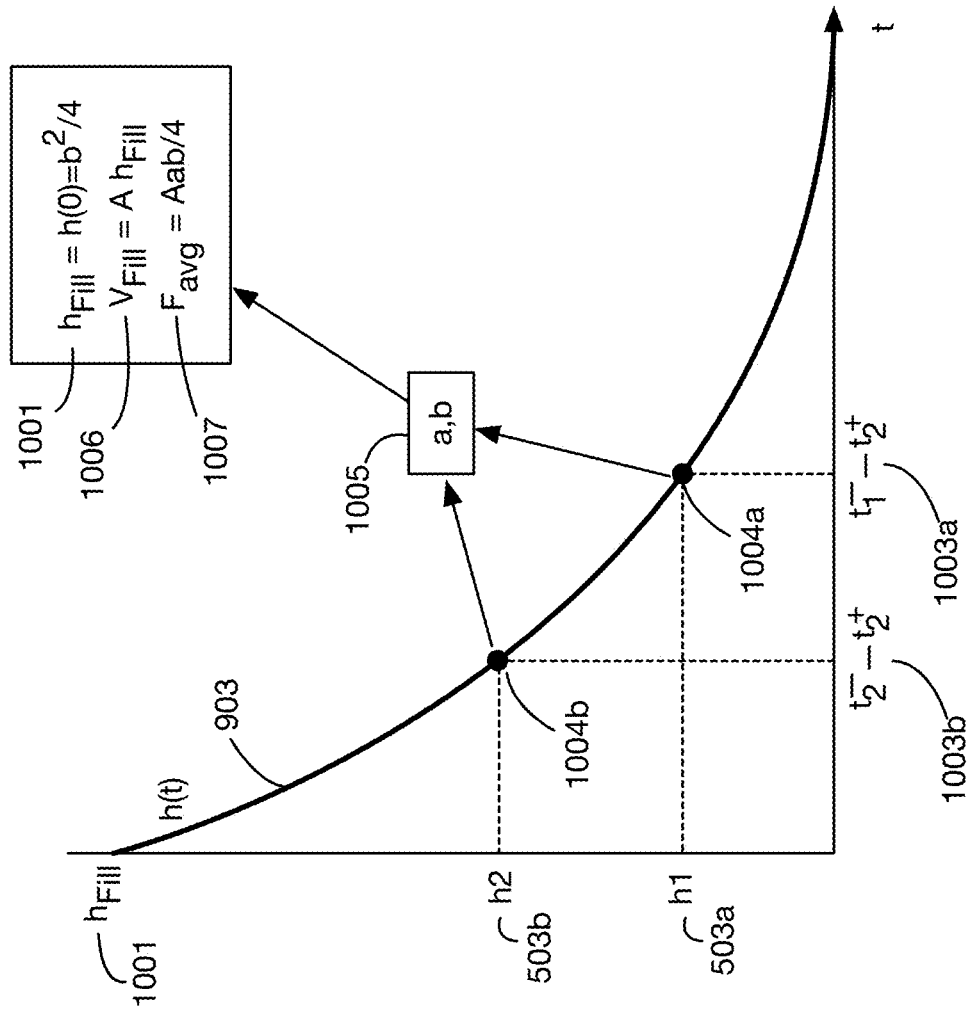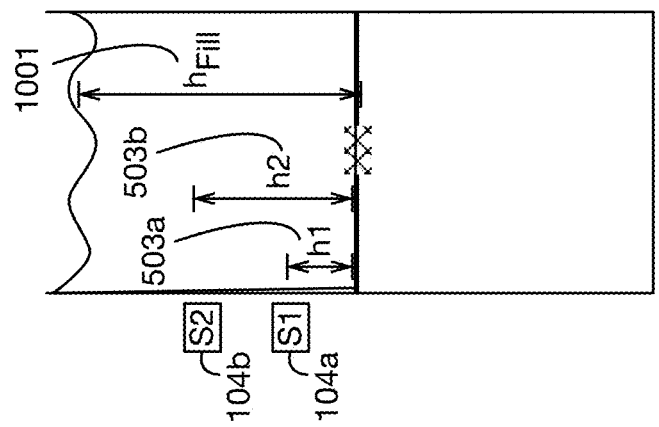
FIG. 10

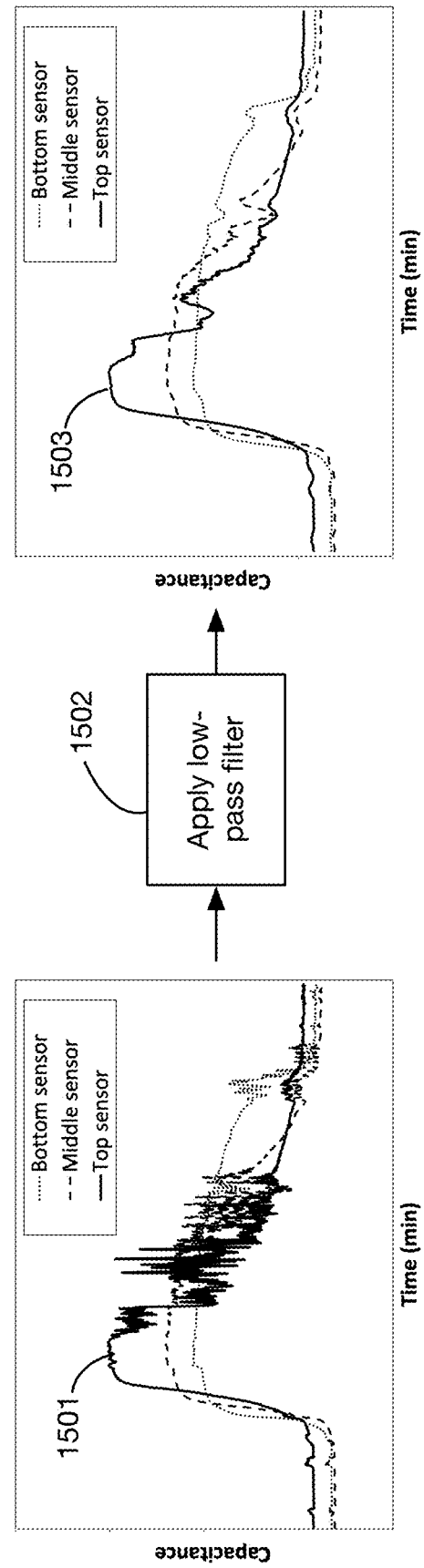

MONITORING AND PERFORMANCE MANAGEMENT SYSTEM FOR A NETWORK OF SMART FILTERING CONTAINERS

This application is a continuation-in-part of U.S. Utility patent application Ser. No. 16/996,818, filed 18 Aug. 2020, the specification of which is hereby incorporated herein by reference.

BACKGROUND OF THE INVENTION

Field of the Invention

One or more embodiments of the invention are related to the fields of liquid filtering and sanitizing devices and data processing systems. More particularly, but not by way of limitation, one or more embodiments of the invention enable a monitoring and performance management system for a network of smart filtering containers.

Description of the Related Art

Filtering containers for water or other liquids are commonly used. For example, some water pitchers may include a built-in filter that can filter regular water. The pitcher may include a hopper to collect the regular water that is poured into the pitcher. The regular water flows through a filter at the bottom of the hopper and into the pitcher reservoir. The filtered water can then be poured out of the pitcher reservoir for consumption.

After a certain amount of water flows through the filter, the filter may get dirty or clogged with impurities and/or no longer remove impurities with sufficient efficacy. To maintain the full benefits of the filter, the filter should be periodically replaced with a new filter. In that regard, both consumers and filter companies like to be notified when the filter should be replaced. To provide such notice, electronics can be incorporated into the pitchers. However, many existing pitchers simply provide a notification to change the filter after a predetermined amount of time, regardless of the amount of water flow and regardless of the filter condition. Other pitchers with sensors may simply detect the number of times a lid to the pitcher is opened, and this method presumes that the user properly fully fills the pitcher each time the lid is opened.

To provide more accurate notifications that a filter should be changed, a filtering container may monitor the actual amount of liquid that flows through the filter. Some filtering containers known in the art use water level sensors integrated into the container. Typically, sensors used for water level sensing include a geometry of vertical sensor strips that often span from the top of the pitcher to the bottom of the pitcher. These strips may sense the level of water in a pitcher by measuring the capacitance between the two vertical sensor strips. The capacitance is dependent on the material surrounding the strips. In an empty container, air is surrounding the strips. In a full container, water is adjacent to the strips. In a partially full container, the capacitance is proportional to the height of the portion of the sensor that is adjacent to the water. Because water has a larger dielectric constant than air, the higher water level results in a larger measured capacitance. Therefore, as the water level increases, the capacitance also increases.

Existing capacitive sensor strips known in the art have several potential disadvantages. First, vertical sensor strips are often located on the inside surface of the pitcher so that the water directly contacts the strips. Although this improves the signal magnitude, such contact between the water and the vertical sensor strips may cause contamination of the water and may alter the taste of the water. Moreover, the vertical sensor strips may degrade, in response to being contacted by the water, and may then contaminate the water. Having the sensors inside the hopper may also require housing the readout electronics inside the hopper or providing electrical feedthroughs to connect the sensors in the hopper to any electronics housed outside of the hopper, both of which add significant points of failure to the system.

Second, because capacitance measurements can be sensitive to small changes in the relative position and geometry of the sensors, using vertical sensor strips to measure the water level typically requires careful calibration of absolute capacitance magnitude against water volume. Third, the measurements will be sensitive to any changes (or drift) in the baseline signal or environmental noise which will create an error in the measured volume. Finally, the use of dual vertical sensor strips pulls the area of maximum sensitivity towards the electrodes, thereby reducing the effectiveness of remote sensing (i.e., sensor strips that are not in contact with the water).

Despite these potential disadvantages of vertical sensor strips, in some applications it is important to continuously monitor the precise level of liquid in a container. This continuous level monitoring may be important for example in applications like gas tanks, or mil vats used by dairy farmers. However, for determining when a filter in a water pitcher should be replaced, it is not important to know the absolute water level in the hopper or pitcher at every moment but rather how much water has passed through the water filter over its lifetime and the flow rate of water through the filter. A vertical sensor strip system may be unnecessary for this purpose. A simpler system that monitors capacitance changes at specific points in time may be sufficient to monitor the flow and volume through a filter.

For containers equipped with sensors, a limitation of existing systems is that the sensor data is used only locally for the specific container from which it was collected. With the emergence of technologies such as "Internet of things", there is an opportunity to combine data from multiple filtering containers, and to form a network of filtering containers that obtains synergies by monitoring many containers simultaneously. Centralizing data and analyses may enable new capabilities such as automated reordering of filters or customizing filter suggestions based on local water conditions. Data may be correlated across containers to provide insights into usage patterns and regional water conditions. There are no known systems that provide this degree of integration across filtering containers.

For at least the limitations described above there is a need for a monitoring and performance management system for a network of smart filtering containers.

BRIEF SUMMARY OF THE INVENTION

One or more embodiments described in the specification are related to a monitoring and performance management system for a network of smart filtering containers. One or more embodiments may manage a network of containers with embedded sensors that measure the state of the container and the liquid that enters and exits the container.

One or more embodiments of the smart filtering containers may include a hopper that receives a liquid, with an inside wall that contacts the liquid and an outside wall that does not contact the liquid. A filter may be coupled to the hopper, and it may remove one or more substances from the liquid as it passes through the filter into a reservoir that stores the filtered liquid. One or more horizontal capacitive sensor strips may be proximal to the hopper. These strips may be located so that they are not in contact with the inside wall of the hopper or with the liquid. In one or more embodiments these strips may not extend vertically across the full height of the liquid in the hopper when the hopper is full.

A processor may receive and process capacitance data from the sensor strips. It may identify points in time in the capacitance data, where each point in time corresponds to an associated height of the liquid in the hopper. It may calculate one or more flow metrics from these points in time.

Although capacitive sensor strips may be of any size and shape, in one or more embodiments each strip may have a horizontal length that is greater than its vertical width.

In one or more embodiments, capacitance data received from the sensor strips may be the self-capacitance of each strip.

In one or more embodiments, the processor may analyze the capacitance data or the flow metrics over a time period to determine when the filter needs to be replaced.

An illustrative flow metric may be for example the flow rate through the filter. In one or more embodiments, this flow rate may be calculated by identifying two points in time in the time series of capacitance data, each corresponding to a height of liquid in the hopper. The flow rate may be calculated based on the time difference between these two points in time, and on the volume difference of the liquid in the hopper between the two corresponding liquid heights. The liquid heights may correspond to the height of two different sensor strips in the hopper, and the points in time may be times when the capacitance of each associated sensor strip is decreasing. Alternatively the two heights may correspond to a top and bottom edge of a single sensor strip, and the points in time may be based on when the capacitance of that single strip begins decreasing, and then stops decreasing.

Changes in flow rate over time may be used to determine when the filter is clogged or needs to be replaced.

In one or more embodiments, the flow rate calculation may be based on a flow rate model, which may be for example either a constant flow rate model or a variable flow rate model. A variable flow rate model may for example assume that the flow rate varies with the height of the liquid in the hopper.

Another illustrative flow metric may be for example the liquid volume added to the hopper when it is filled. This volume may be calculated based on a filter flow rate, possibly using a flow rate model that may be constant or variable, and on a time difference between a time when capacitance of one of the sensor strips is increasing (during filling, for example), and when it is decreasing (during filtering, for example). One or more embodiments may track the total amount of liquid added to a hopper over a time period to determine when the filter needs to be replaced.

In one or more embodiments the horizontal capacitive sensor strips may be in a sensing package that can be attached to or detached from the outside wall of the hopper. The strips may be inside a housing of the sensing package. In one or more embodiments the outside wall of the hopper may mate with the sensing package when it is attached to the hopper.

In one or more embodiments, the processor may transmit a message or a command based on the capacitance data. For example, it may activate an ultraviolet light that may direct ultraviolet radiation toward one or more of the hopper, the filter, the reservoir, the liquid, and the filtered liquid.

One or more embodiments may include or interface with additional sensors, such as a motion sensor for example. The processor may analyze motion sensor data to determine whether changes in capacitance data are due to motion of the container.

One or more embodiments of the invention may include multiple smart filtering containers that are coupled via network connections to a processor. Each smart filtering container may have a hopper that receives a liquid (such as water), a filter coupled to the hopper, and a reservoir that receives and stored filtered liquid that passes through the filter. The filter may remove one or more substances from the liquid. Each container may also include one or more sensors that measure one or more characteristics of the liquid, the filtered liquid, the filter, the hopper, the reservoir, the flow of liquid into the hopper, the flow of liquid through the filter, or the flow of filtered liquid from the reservoir. Each container may have a controller that is coupled to the sensors and to a network interface; the controller may transmit measurements based on sensor data over the network interface.

The processor may receive the measurements from the smart filtering containers. It may analyze these measurements to identify one or more of the containers for which a performance modification is desired. For each of these containers, it may transmit a message based on the desired performance modification. The message may be for example a settings message, and order message, a usage message, or an information message. A settings message may set or modify an operational parameter of the associated smart filtering container. An order message may order an item associated with the smart filtering container. A usage message may instruct a user of the container to modify the usage of the container. An information may provide information related to the liquid, the filtered liquid, the user, or the container.

Analysis of measurements from the smart filtering containers may for example calculate one or both of the flow rate through the filter, or the cumulative volume of liquid filtered through the filter. Based on these calculations, a desired performance modification may be for example replacement of a filter that is clogged, slow, defective, or at or near its expected life. Messages associated with this performance modification may include for example an order message for a replacement filter, or a usage message that recommends filter replacement to the user.

Analysis of measurements may for example determine the water quality of the liquid or the filtered liquid. Messages based on water quality may include for example an information message on the water quality transmitted to the user or to an organization that monitors or affects water quality, an order message for a water quality test, or an order message for a replacement filter that is configured for the measured water quality. One or more embodiments may correlate water quality with container locations to determine the water quality in one or more regions.

One or more embodiments of the invention may access external data and may use this external data to identify containers for which performance modifications are desired. For example, the processor may obtain information on local water conditions for one or more regions in which the smart filtering containers are located, and may transmit messages based on these conditions. Messages may include for example an information message on the water conditions transmitted to the user or to an organization that monitors or affects water conditions, an order message for a water quality test, or an order message for a replacement filter that is configured for the local water conditions.

In one or more embodiments, the smart filtering containers may have one or more actuators. For example, they may have a sanitization actuator that sanitizes one or more of the liquid, the filtered liquid, or the filter. An illustrative sanitization actuator may be an ultraviolet light source that sanitizes by emitting ultraviolet radiation. A settings message may modify the duration, schedule, or intensity of the ultraviolet radiation; these modifications may be based on information on local water conditions.

Analysis of measurements may include estimating the amount of liquid dispensed over a period of time from one or more of the smart filtering containers. If that amount is below a threshold value, a usage message may be sent recommending an increase in liquid consumption, or an information message may be sent to a person or organization associated with the user to alert them that the user is not consuming sufficient liquid.

One or more embodiments of the invention may include a testing application that executes on a device used by the user. This application may capture an image of a test that the user has exposed to the liquid or the filtered liquid. The test may change appearance based on one or more substances that may be present in the liquid or the filtered liquid. Image information from the captured image may be sent to the processor for analysis. The test may have a test region that changes appearance based on the substances in the liquid or filtered liquid, and one or more reference regions that have reference colors. Results from the analysis of the test image may be used to send an information message to the user or to an organization that monitors or influences water quality, or an order message for a replacement filter that is configured for the tested water quality. The processor may also correlate water quality with locations to determine the water quality in one or more regions.

BRIEF DESCRIPTION OF THE DRAWINGS

The above and other aspects, features and advantages of the invention will be more apparent from the following more particular description thereof, presented in conjunction with the following drawings wherein:

FIG. 10 shows an illustrative calculation of the volume of liquid added to the hopper of a container using the flow rate model of FIG. 9.

FIG. 15 illustrates filtering of the capacitance data from sensor strips to remove the effect of motion on the data when the container is moved during filtering.

DETAILED DESCRIPTION OF THE INVENTION

A monitoring and performance management system for a network of smart filtering containers will now be described.

In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
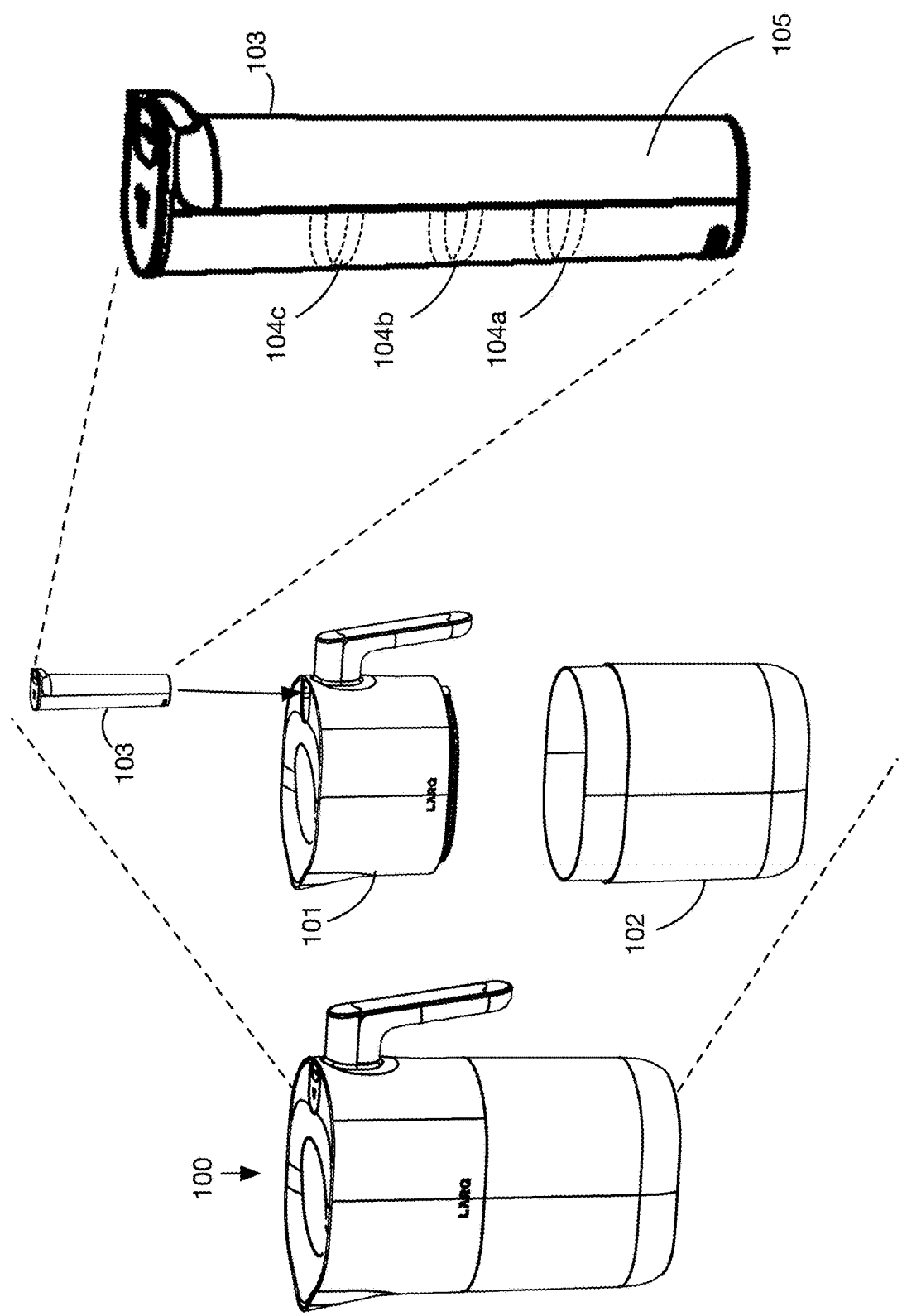
FIG. 1 shows an illustrative container with a filter, which includes an electronics module containing horizontal capacitive strips that are used to sense flow of liquid through the filter.

FIG. 1 shows an illustrative filtering container 100, and an exploded view of container 100 which includes a hopper 101 into which a liquid is poured, and a reservoir 102 that receives filtered liquid exiting the hopper 101. A filter or filters of any type may be placed between hopper 101 and reservoir 102 (or it may be integrated into either or both of the hopper or the reservoir); the filter may remove one or more impurities from the liquid as it passes from the hopper to the reservoir. For example, without limitation, the container 100 may be a portable water pitcher with an integrated filter.

Container 100 may also contain a sensing package 103 that may include sensors or other electronics. In the embodiment shown in FIG. 1, sensing package 103 is a "wand"-shaped component that can attach to hopper 101 by sliding into a corresponding indentation in the hopper; the wand can be removed for example for cleaning of the container, so that the electronic components in the wand are not exposed to hot water or steam during cleaning. In one or more embodiments, the sensing package may be integrated into the hopper 101 directly. Sensing package 103 may have various electronic components enclosed in a housing. In one or more embodiments, the housing of sensing package 103 may be constructed of a plastic material such as for example Tritan™ plastic, SMMA (styrene methyl methacrylate), SAN (styrene acrylonitrile resin), or PC (polycarbonate). FIG. 1 shows a close-up view of an embodiment of sensing package 103. Within a plastic enclosure 105, sensing package 103 contains three capacitive sensor strips 104a, 104b, and 104c. These strips may be used in one or more embodiments to measure flow of liquid into and out of hopper 101, as described below. These strips detect liquid via its effect on capacitance; since the dielectric constant of water for example is much higher than that of air, a capacitive strip in the proximity of water will have a higher capacitance than one near an empty part of a hopper. One or more embodiments may contain any number of capacitive sensor strips, including but not limited to the three strips shown in FIG. 1. The sensor strips may be of any size, shape, spacing, and orientation. They may be made of any material, including for example copper or other metals. The sensing package 103 may also contain additional components such as a processor, a power supply, other types of sensors, actuators, and communications interfaces. Sensors may for include for example, without limitation, an accelerometer, a light sensor, a sound sensor, a pressure sensor, a presence sensor, a temperature sensor, a humidity sensor, a pH sensor, a TDS sensor, or a salinity sensor. Communications interfaces may include for example, without limitation, Bluetooth, Bluetooth Low Energy, Wi-Fi, or any other wired or wireless networking technology or protocol. Actuators may include for example, without limitation, lights, displays, speakers, or vibration actuators.

The capacitive sensor strips 104a, 104b, and 104c are enclosed in housing 105, and the entire sensing package 103 is installed along the outside wall of hopper 101. The sensing strips therefore may not make direct contact with the liquid in hopper 101. Moreover, there may be multiple layers of air and wall or housing material between the liquid and the sensor. Although liquid levels in the hopper 101 still affect the measured capacitance of the sensing strips, the signals may be relatively weak or noisy due to the layers between the strips and the liquid. As described below, in one or more embodiments the capacitance signals may be processed to provide reliable flow metrics despite the layers between the sensors and the sensed liquid.

The capacitive sensor strips may be placed in any locations with any amount of spacing between the strips. Spacing between strips need not be uniform. In an illustrative embodiment, the bottom of the first horizontal sensor strip 104a may start at 1 inch from the bottom of the wand 103, and the bottom of the second horizontal sensor strip 104b may start at 2 inches from the bottom of the wand 103 (with 1 inch between these horizontal sensor strips). Sensor positioning and spacing may be selected to optimize sensitivity and coverage of possible liquid levels. For example, if the sensors are too close together, they can interfere with one another. If they are spaced too far apart, the upper sensors may not be triggered if the water level in the hopper does not reach a sufficient level above the sensor. Capacitive sensor strips may be of any shape or size.

Figure 2:
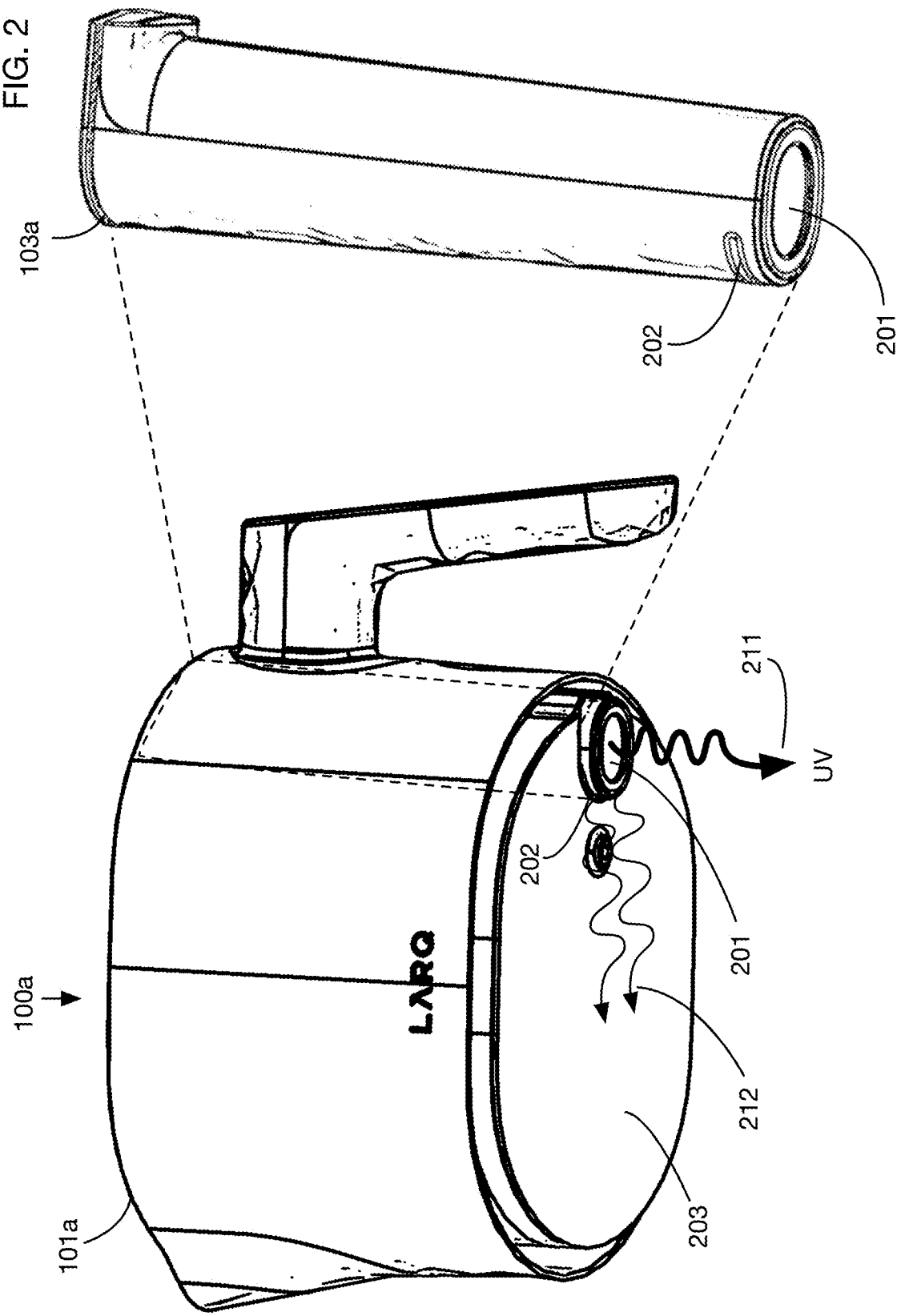
FIG. 2 shows an illustrative embodiment with an ultraviolet light source that may be used for sanitizing the liquid in the container or sanitizing portions of the container.

In one or more embodiments, the filtering container may also include one or more means for sanitizing one or more of the liquid, the filter, the hopper, and the reservoir. For example, one or more embodiments may use ultraviolet (UV) light to sanitize any or all of these items. FIG. 2 shows a hopper 101a of an illustrative embodiment 100a, with a wand 103a installed in the hopper. The wand 103a contains an ultraviolet light source that direct ultraviolet radiation 211 through a window 201 at the bottom of the wand, towards the liquid in the reservoir below the hopper. The UV light source may be activated based for example on data received from the capacitive sensor strips, on data from other sensors, or on commands received from external controllers (such as a user's phone), or in response to user input via switches or buttons on the container or the wand. For example, in one or more embodiments, capacitive sensor data may be processed to determine when the container has been refilled, and when the refilled liquid has passed through the filter into the reservoir; the UV light source may then be activated to sanitize the liquid in the reservoir after it has been filtered. In one or more embodiments, the UV light source may be activated after a certain cumulative amount of liquid has been filtered through the filter, or for example to periodically sanitize the filter itself or the hopper or reservoir or any liquid held in the reservoir. In one or more embodiments, the UV light source may be activated periodically after a certain period of time, independent of the amount of liquid that has been filtered.

One or more embodiments may apply UV light to sanitize any type of vessel, including those without filters. These vessels may or may not have capacitive sensor strips or other sensors to detect when liquid is added to or removed from the vessel. Illustrative examples include water bottles, water dispensers, and medical or laboratory containers of fluids.

In the embodiment shown in FIG. 2, the wand 103a also has a side-facing window 202, through which visible light 212 may be emitted. This light 212 may for example be injected into a clear waveguide 203, causing this waveguide 203 to light up, flash, or change color when light 212 is emitted. This capability may be used for example to provide one or more visible signals to users, to communicate status or activity or to prompt users to perform certain actions.

Figure 3:
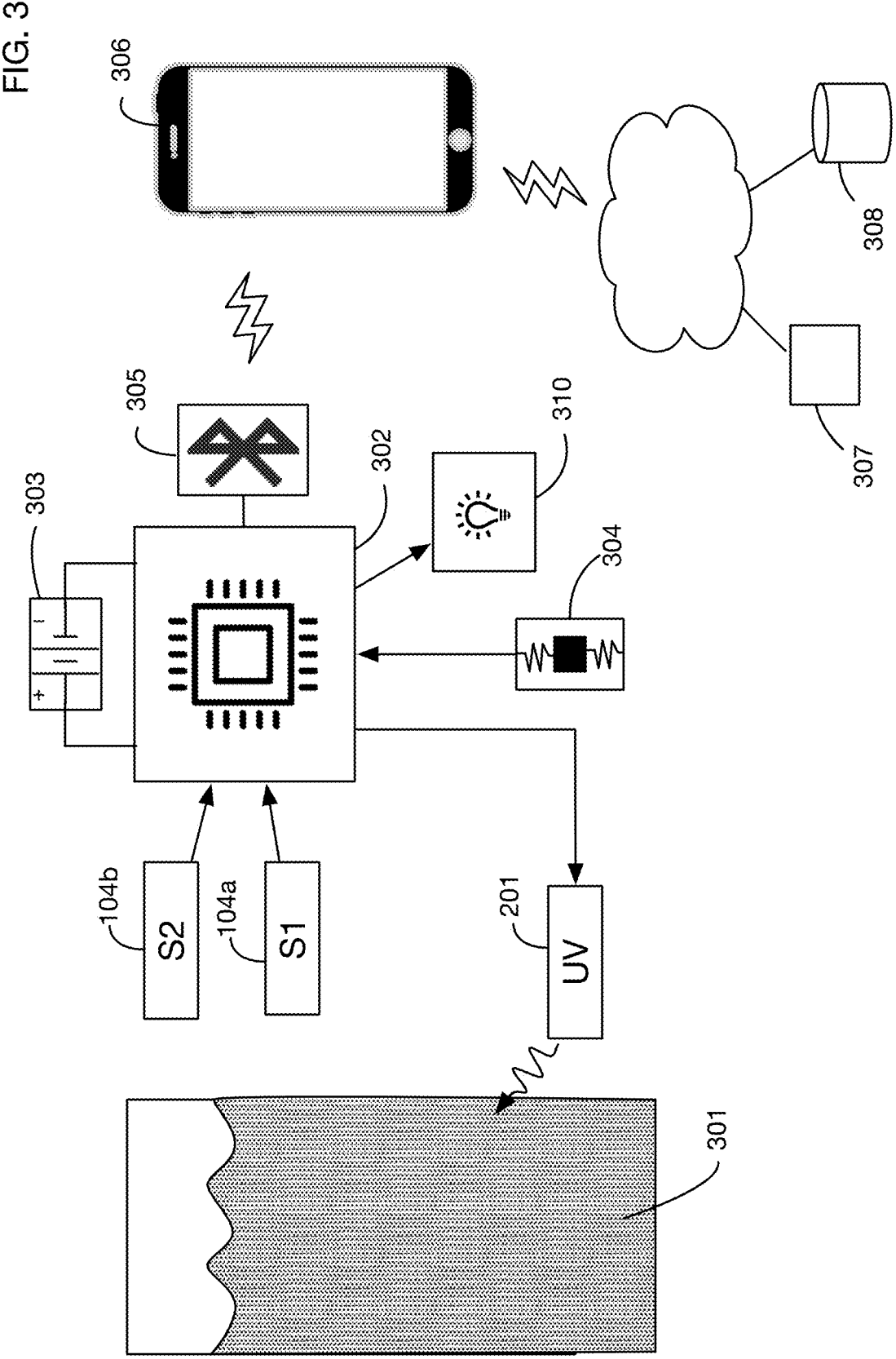
FIG. 3 shows a block diagram of the sensing, processing, and communication components of an embodiment of the invention.

FIG. 3 shows a block diagram of illustrative electronic components in one or more embodiments of the invention. Some or all of these components may be contained in a removable module such as sensing package 103 shown in FIG. 1. In some embodiments, not all of these components may be present. Some embodiments may have additional components beyond those shown in FIG. 3. Illustrative components include capacitive sensors such as sensors 104a and 104b, which sense changes in the level of liquid 301 in the filtering container; any number of these capacitive sensors may be present. A processor or processors 302 may receive data from these capacitive sensors; the processor 302 may include any auxiliary components or circuits such as signal filters, digital signal processors, and volatile or non-volatile memory. Processor or processors 302 may include for example, without limitation, any type of microprocessor, microcontroller, ASIC, CPU, GPU. An illustrative processor that may be used in one or more embodiments is a Texas Instruments® FDC 1004 processor. A power source 303, such as a battery, a solar power source, or any source of energy, may power processor 302 as well as other components. A port for recharging the power source (or for powering components from an external power source) may also be provided in one or more embodiments. Processor 302 may also be connected to actuators such as UV light source 201, and to other sensors such as an accelerometer 304, a light sensor, a sound sensor, a pressure sensor, a presence sensor, a temperature sensor, a humidity sensor, a pH sensor, a TDS sensor, a salinity sensor, or any other type or types of sensors. Processor 302 may be connected to a communications interface or interfaces 305, which may include for example wireless interfaces that transmit data over Bluetooth or Wi-Fi links. Data may be transmitted for example to or from devices 306 such as a phone, a laptop computer, a tablet computer, a notebook computer, a desktop computer, a server, or any combination or network of these devices. These devices may further process sensor data or other signals. Information may be displayed to user, for example to indicate when a filter should be replaced.

In one or more embodiments, processor 302 may be connected to one or more indicators 310, such as lights, displays, speakers, or vibration actuators, which may be controlled to provide status indications or messages to a user (such as a light while liquid is being filtered, or a flashing light that indicates that a filter should be replaced or inspected). An indicator may explain, respond to, or activate a trigger. Triggers may include for example changes or thresholds related to flow rate, filter life, impurity data, changes or trends or thresholds in data from any sensor associated with the container, comparisons of system data to industry data, latest trends, historical data, calorie count, weight management data, pending notifications. A visual indicator may include a display screen that displays for example graphs, data, text, symbols, graphics, updates, data feeds, goals, comparisons, or competitions. For example, the display may provide a graph or data about flow rate, filter life, impurity data, comparisons of system data to industry data, latest trends, historical data, calorie count, or weight management data. A visual indicator may also include a light (e.g., LED). The light may be a circle, a light bar and/or a light strip that partially or fully extends around the filtering container. The light strip may be located on any part of the container. For example, the light strip may be located near the center of the container and wrap around the entire circumference. The light may turn on/off, change colors, flash, strobe, rotate colors, travel around a path, etc., in response to certain triggers. An audible indicator may include, for example, a recorded voice, synthetic voice, beep, different combinations of beeps or any other sound. A physical indicator may include, for example, a vibration.

In one or more embodiments, data may be transmitted from devices 306 to one or more services 307 or databases 308, for example to record usage information or to order replacement filters automatically when needed. In one or more embodiments, the processor 302 may transmit data to or from services 307 or databases 308 directly, without using an intermediary device 306. Services 307 and databases 308 may for example include websites, apps, social media sites or services (such as FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®), affiliate or partner websites (such as AMERICAN EXPRESS®, GROUPON®, LIVINGSOCIAL®), other pitchers, Internet-of-Things devices, consumer devices (such as APPLE TV®, MICROSOFT® XBOX®, ROKU®, AMAZON FIRE®, GOOGLE CHROMECAST®, SONY® PLAYSTATION®, NINTENDO® SWITCH®), and central databases. The data may include water quality readings, total dissolved solids (TDS), acidity or PH, or notifications to change the filter. The data may also include parameter extractions from the raw data such as, for example, total volume processed, flow rate, change in flow rate, etc. The data may also include information about optimal filter changes in different regions, during different seasons or during different time frames. The system may automatically determine when the existing filter drops below a certain flow rate, then the system may send a notification via a communication channel (e.g., text, email, website, social media, smart digital assistant, etc.) to facilitate placing an order for a new filter. The system may monitor the number of replacement filters available to a user, then place an order for new replacement filters when the stock of filters is running low.

Services 307 may include one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with the novel pitcher system by also allowing for ordering of new filters, playing music, reading emails, reading texts, making phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices for ordering additional filters or other products/accessories.

Figure 4:
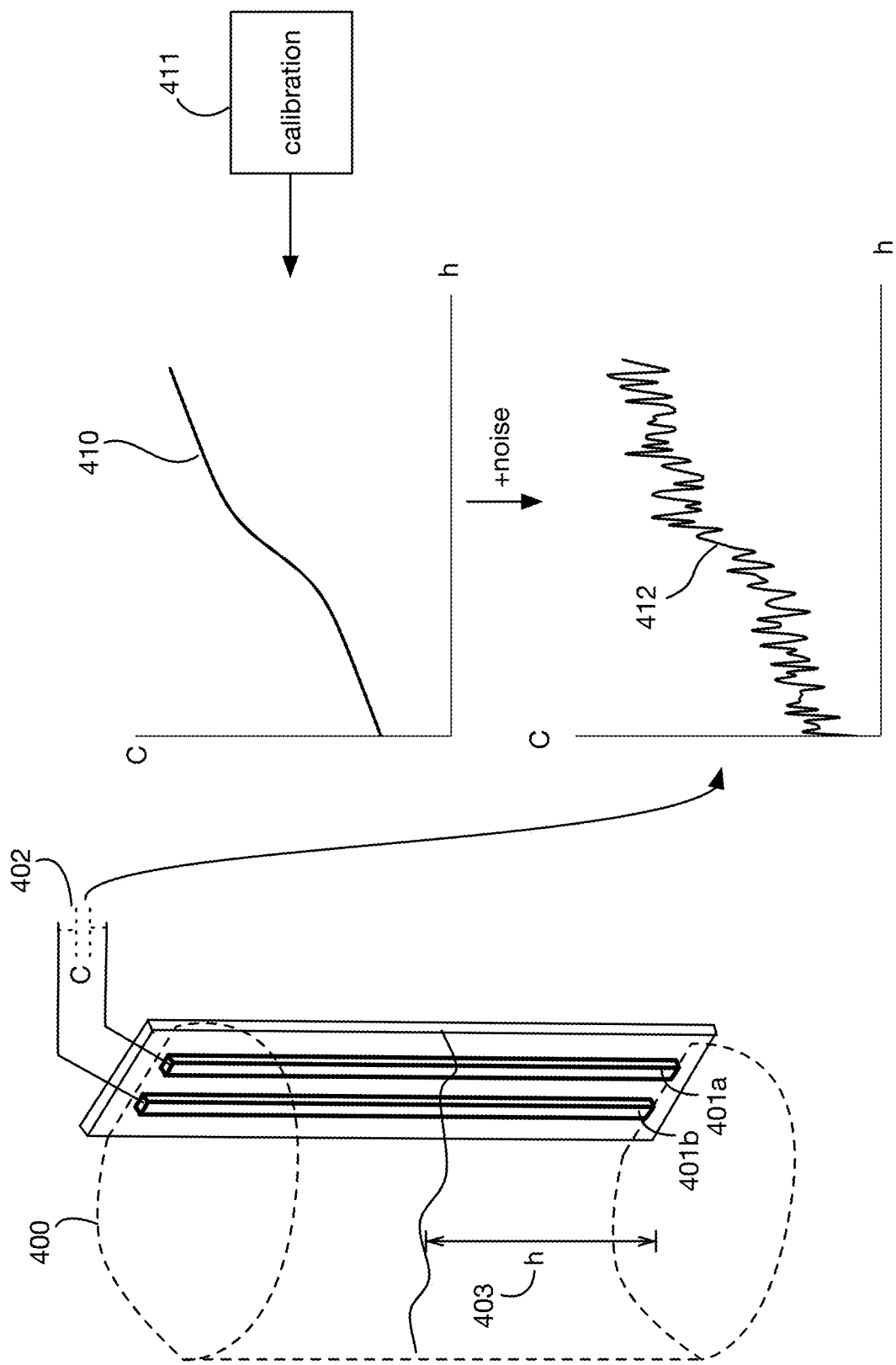
FIG. 4 shows an illustrative flow monitoring device used in the prior art, which uses parallel vertical capacitive strips to monitor the level of a liquid in a container.
Figure 5:
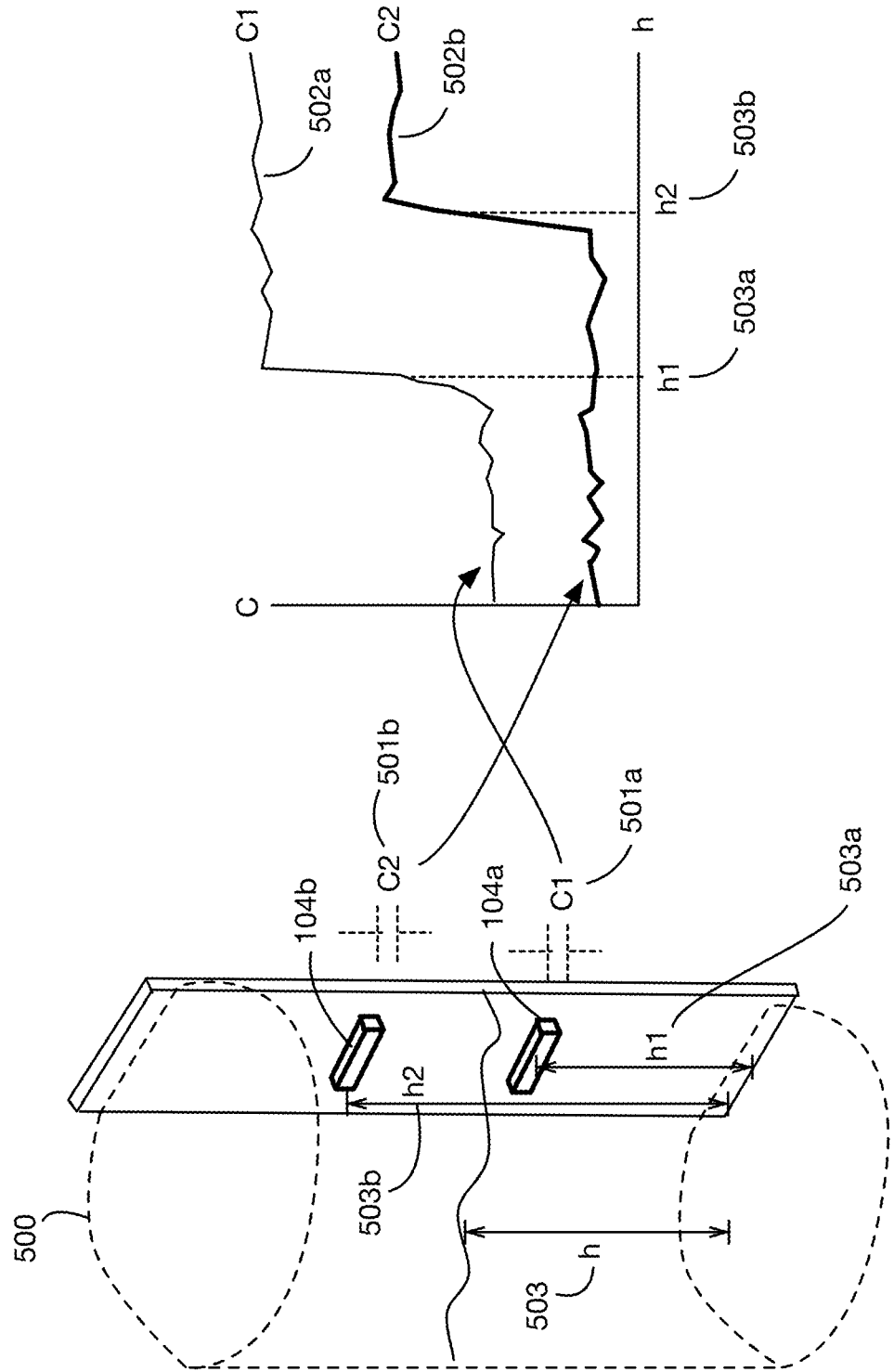
FIG. 5 shows a flow monitoring device used in one or more embodiments of the invention, which uses one or more horizontally oriented capacitive strips to detect when a liquid reaches particular levels; this approach is more robust than the approach illustrated in FIG. 4.

FIGS. 4 and 5 contrast a method used in one or more embodiments of the invention to calculate flow metrics to an approach used in the prior art based on vertical capacitor strips. FIG. 4 shows the vertical strip technique used in the prior art. Two parallel vertical capacitive strips 401a and 401b may be placed along a wall of a liquid container 400, and the capacitance 402 between these strips may be measured. This capacitance generally changes as the height 403 of the liquid in the container changes; as the liquid level rises, the capacitance also increases. Containers in the prior art that use this technique typically attempt to estimate the height 403 of the liquid continuously (or frequently) from the capacitance signal 402. Flow rates are then calculated from changes in the height 403. This approach presents at least two challenges. First, the relationship 410 between liquid height 403 and capacitance 402 may be a complicated nonlinear curve, due for example to variations in container shape, variable spacing between the vertical strips, or other physical variations. A calibration procedure 411 may therefore be required to determine this curve 410 for each container; recalibration may also be necessary periodically as the physical and electrical characteristics of the container and the strips change over time. Second, the capacitance signal 402 may be influenced significantly by noise; therefore the actual relationship 412 between capacitance and liquid height at any point in time may deviate significantly from the calibration curve 410. As a result, estimates of liquid height from capacitance may have significant errors or uncertainties.

FIG. 5 shows an approach to measuring flow metrics employed in one or more embodiments of the invention. Instead of vertical strips such as strips 401a and 401b of FIG. 4, the illustrative container 500 has one or more horizontal capacitive strips such as strips 104a and 104b. These strips may be of any shape and size, and there may be any number of these horizontal strips. A key difference between the approach shown in FIG. 5 and that of FIG. 4 is that the capacitive strips in FIG. 5 do not extend vertically along the entire container 500 (or along the entire portion of this container for which it is desired to measure liquid flow, such as the hopper portion 101 of the container 100 of FIG. 1). In one or more embodiments the strips 104a and 104b may extend horizontally along a wall of the container 500, and their horizontal dimension may be greater than their vertical dimension; this may not be the case in some embodiments, however. Another difference between the approach illustrated in FIG. 4 and that shown in FIG. 5 is that in one or more embodiments of the invention, the self-capacitance of each sensor strip may be measured to detect liquid changes, as opposed to the mutual capacitance 402 measured in FIG. 4 between the two vertical strips 401a and 401b. This use of self-capacitance may simplify wiring, for example, since only a single conductor may be needed for each horizontal capacitive strip. This self-capacitance may be measured with respect to any convenient ground level; for example self-capacitance 501a may be measured for strip 104a, and self-capacitance 501b may be measured for strip 104b.

Because the horizontal capacitive strips 104a and 104b do not extend vertically along the container 500, the corresponding capacitances 501a and 501b do not vary linearly with the height 503 of the liquid in container 500. Instead, these capacitances change rapidly as the liquid level 503 passes by the corresponding height of each strip. Illustrative curves 502a and 502b show the changes in capacitance 501a and 501b, respectively, as a function of liquid height 503. The zones of rapid change in capacitance correspond to the heights 503a and 503b of the sensors 104a and 104b, respectively. The magnitude of the capacitance change is generally dependent on the surface area of the horizontal strip, which (for a rectangular strip) is the product of the vertical width of the strip and its horizontal length. A narrower strip (with a smaller vertical width) provides a sharper time transition because the liquid level passes from one edge of the strip to the other in less time. However, if the total surface area of the strip is small, the change in capacitance as the liquid passes from one edge of the strip to the other may be relatively small, may make it more difficult to locate the transition. By increasing the horizontal length of the strip, the capacitance can be increased to compensate for a smaller vertical width. Therefore one or more embodiments may use capacitive sensor strips with horizontal lengths that exceed their vertical widths, in order to achieve sharper transitions without reducing total capacitance.

The relative heights of the capacitance curves 502a and 502b are illustrative; in one or more embodiments the upper capacitive strip 104b may have either a higher capacitance or a lower capacitance than the lower capacitive strip 104a. Relative capacitances may depend for example on the local environment of the sensors, such as the distance from the sensor strips to conductive or insulating surfaces, the presence and volume of water in the post-filter reservoir, or the presence or detailed composition of the filtering media. The relative levels between the two capacitive strips are not used; instead only the transition regions for each capacitance curve are used to identify when the liquid level passes the level of each capacitive strip.

Although the capacitance signals 502a and 502b may be noisy, like the capacitance 412 of the vertical strips of FIG. 4, the transitions as the liquid height passes heights 503a and 503b are distinct and can be detected easily despite the noise. One or more embodiments of the invention may therefore use these transition points to calculate flow metrics for the flow of liquid in container 500. This approach may be more robust and effective than the approach described with respect to FIG. 4. In a sense the "analog" measurement of liquid height in the embodiment shown in FIG. 4 is replaced with a "digital" approach in one or more embodiments of the invention, with a resulting improvement in reliability and robustness. As an additional benefit, it may not be necessary to calibrate the capacitance curves 502a and 502b, since detection of the transition points 503a and 503b is possible without knowing the calibration of the entire curves; the absolute values of the capacitance are not used directly so calibration is not required. Also, detection of transition points and processing of the resulting "digital" data may be simpler than the continuous processing of capacitance data in a vertical sensor strip configuration like that described with respect to FIG. 4; the processor complexity and power consumption of this approach may therefore be lower, resulting in lower cost filtering containers.

Figure 6:
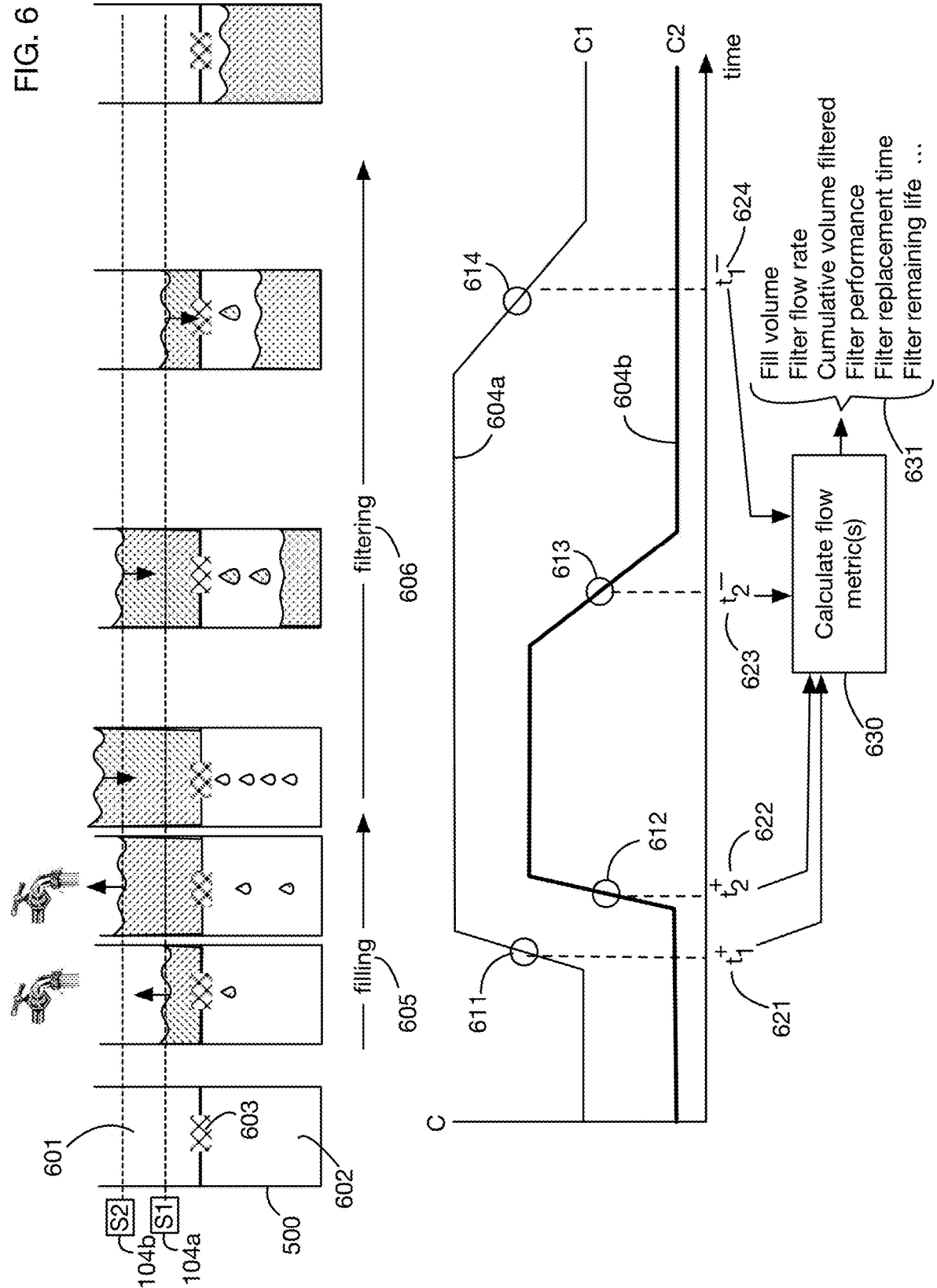
FIG. 6 shows illustrative graphs of capacitance measured by the sensors shown in FIG. 5 as a liquid is filled into the hopper of a container and then filtered into the container's reservoir, and illustrative calculation of flow metrics from points in time on the capacitance curves.

FIG. 6 shows capacitance curves over time 604a and 604b, for capacitances measured by horizontal capacitive strips 104a and 104b, respectively, as a liquid is filled into hopper 601 of filtering container 500, and then passes through filter 603 into reservoir 602 of the container. Filter 603 may be any type of assembly that may remove impurities or otherwise process a liquid; for example, in one or more embodiments it may include filter media as well as a flow restrictor. There is an initial filling phase 605, followed by a filtering phase 606. (A small amount of filtering may occur during the filling phase as well, and may need to be corrected for.) Analysis of the curves 604a and 604b may identify specific points in time that correspond to specific events in the filling and filtering phases; these points in time may then be used in calculation 630 of one or more flow metrics. Illustrative calculations are described below with respect to FIGS. 8 through 12.

FIG. 6 shows illustrative points in time 621, 622, 623, and 624 in capacitance curves 604a and 604b, which may be input into flow metric calculations 630. These points in time may for example correspond to times when the liquid levels in hopper 601 transition past the corresponding heights of sensors 104a and 104b. Time 621 corresponds to event 611 when capacitance 604a is increasing. This time may be anywhere on or near the rising edge of the corresponding capacitance curve, not necessarily in the midpoint of this rising edge. Similarly, time 622 corresponds to event 612 when capacitance 604b is increasing; this time 622 may be anywhere on or near the rising edge of the capacitance curve 604b. Time 623 corresponds to event 613 when capacitance 604b is decreasing, and time 624 corresponds to event 614 when capacitance 604a is decreasing; these times may be anywhere on or near the falling edges of the corresponding capacitance curves. As described below, the time intervals between these identified points in time may be used in calculations 630 to calculate flow metrics that indicate for example the rate at which liquid flows through the filter 603, the total volume of liquid added to the hopper 601, or the rate at which the hopper is filled. Any desired metrics may be calculated from this data, or from trends in this data over time; these metrics may include for example, without limitation, the fill volume (total volume added to the hopper), the fill rate at which liquid is added to the hopper, the filter flow rate, the cumulative volume filtered through the filter over a time period, measures of filter performance, filter replacement times or indicators, and estimates of filter remaining life.

Figure 7:
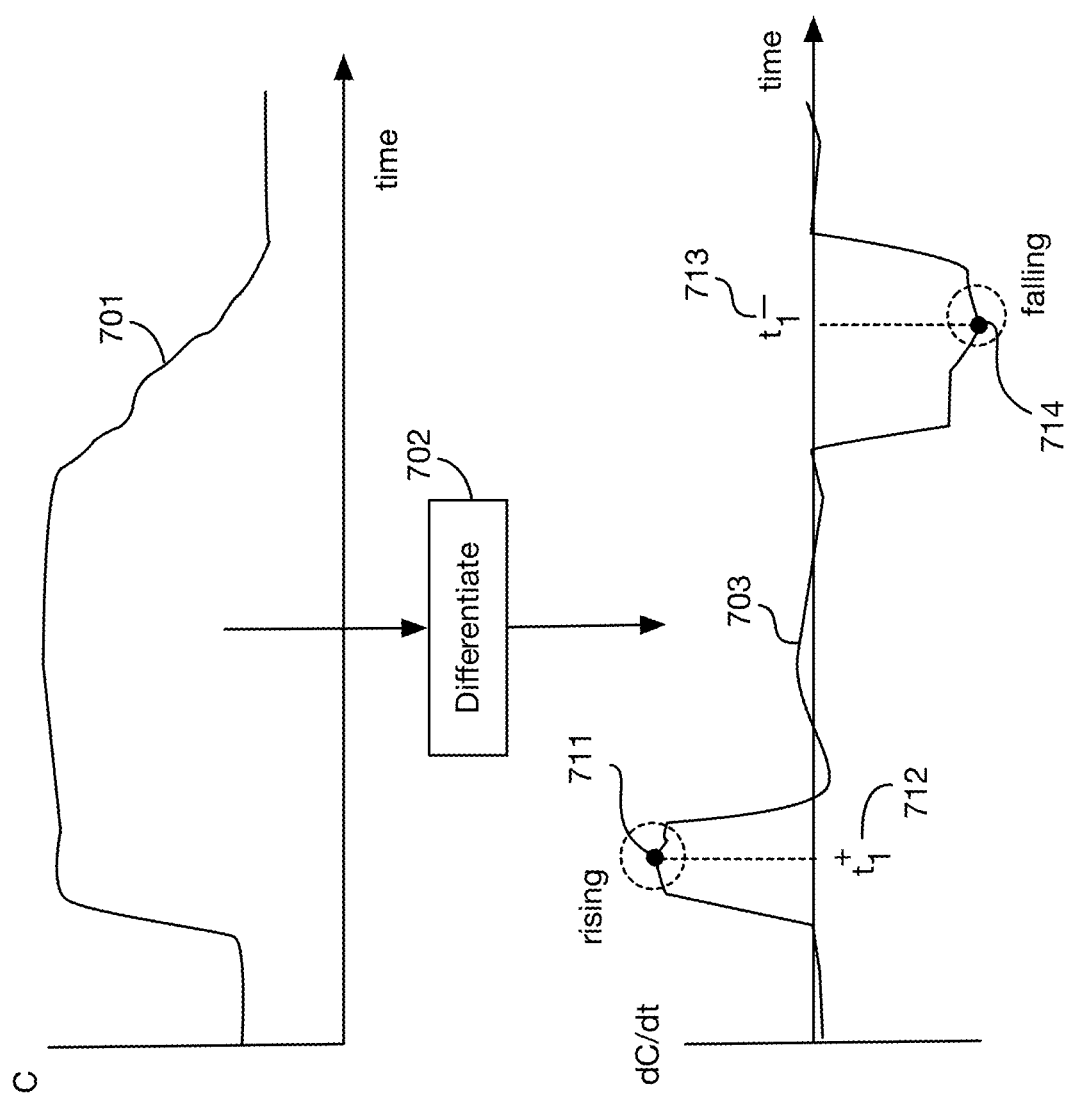
FIG. 7 shows identification of points in time of interest in the capacitance curves by looking for peaks in the curves' derivatives.

FIG. 7 shows an illustrative technique that may be used in one or more embodiments to identify some or all of the points in time that may be used to calculate flow metrics. Illustrative capacitance curve 701 shows the capacitance over time for an illustrative horizontal capacitive strip. To find points on the leading and trailing edge of this curve, one or more embodiments may apply a differentiation operation 702 to the curve 701 to obtain a capacitance derivative curve 703. A maximum point 711 on this derivative curve 703 may be located to find a time 712 on the rising edge of the capacitance curve (during filling of the hopper), and a minimum point 713 may be located to find a time 714 on the falling edge of the capacitance curve (during filtering). In one or more embodiments, smoothing or other filtering operations may be applied before or after differentiation 702. The calculation of derivatives may be accomplished using software and/or hardware. Use of derivatives helps to eliminate DC offsets and highlights transitions (e.g., fill points and when the water level crosses a sensor strip). DC offsets may include, for example, the wearing down of the electrodes, electrical noise that impacts the system, metal objects such as appliances near the electrodes, etc. For example, while a maximum capacitance level may have been 15 pF in the past, these offsets may cause the maximum capacitance level on the same system to drift to only 12 pF. A system relying on absolute measurement would then need to somehow correct for this. However, embodiments of the invention may be insensitive to this drift since they may look only for changes in amplitude (e.g., a sudden rise in capacitance during filling, followed by a less sudden fall in capacitance during filtering).

Figure 8:
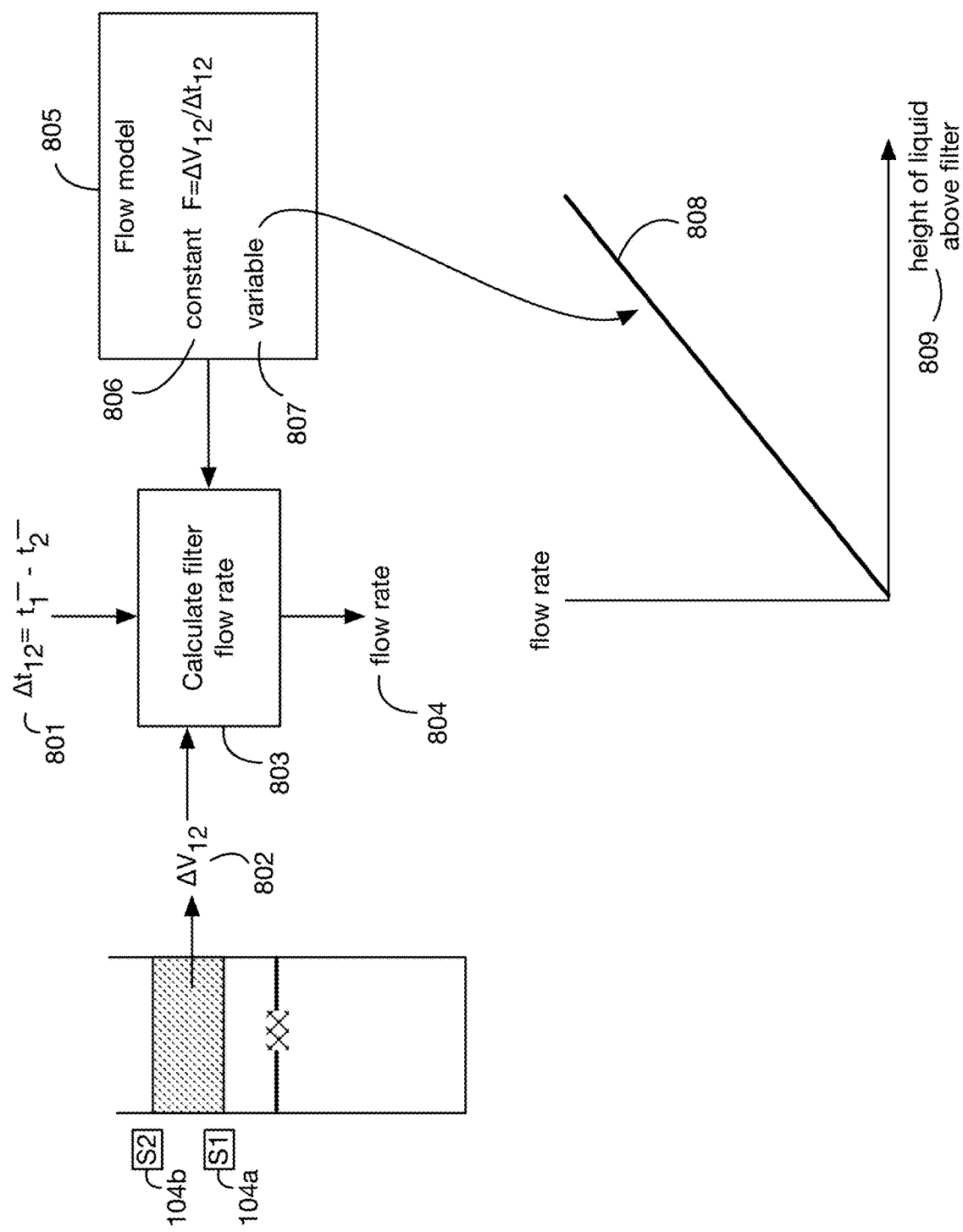
FIG. 8 shows calculation of filter flow rate, an illustrative flow metric, based on the volume of liquid between two horizontal sensor strips and on the points in time that the liquid level passes the position of each of the two strips as it is filtered.

FIG. 8 shows illustrative calculation of a flow rate through the filter from the time difference 801 between the falling edge timepoints of two horizontal capacitive strips 104a and 104b. Since the falling edge time associated with a sensor corresponds at least approximately to the time the liquid height in the hopper transitions past the corresponding height of the sensor, a fixed volume 802 of liquid flows through the filter between the time the liquid reaches the height of the upper sensor 104b and the time it reaches the lower sensor 104a. Using this volume difference 802 and the time 801 required to filter this volume, a calculation 803 can determine the flow rate 804 through the filter. In one or more embodiments, this calculation 803 may be based on a flow model 805 that describes factors that affect the flow rate. A simple constant flow model 806 may for example treat the flow rate through the filter as constant over a short period of time; in this case the flow rate may be calculated as the volume change 802 divided by the time 801. One or more embodiments may use or calculate more complex models 807 with variable flow rates that vary for example as the height of the liquid above the filter changes. For example, one or more embodiments may use a flow rate model where the flow rate 808 through the filter varies linearly with the height 809 of the liquid above the filter. A variable flow rate model may for example assume that the pressure of the liquid on the filter varies with the weight of the liquid, which varies linearly with the height if the hopper has a constant cross sectional area. One or more embodiments may use or derive other variable flow rate models with nonlinear relationships between height and flow rate, or models where the flow rate varies based on additional factors such as temperature, atmospheric pressure, or liquid composition.

Via a calculation similar to 806, which estimates the flow rate through the filter by dividing the known volume 802 between the two sensor strips by the time difference 801 between the falling edges of the capacitance curves, one or more embodiments may calculate the rate at which the hopper is filled by dividing the volume 802 by the time difference between the leading edges of the capacitance curves (612 less 611).

Figure 9:
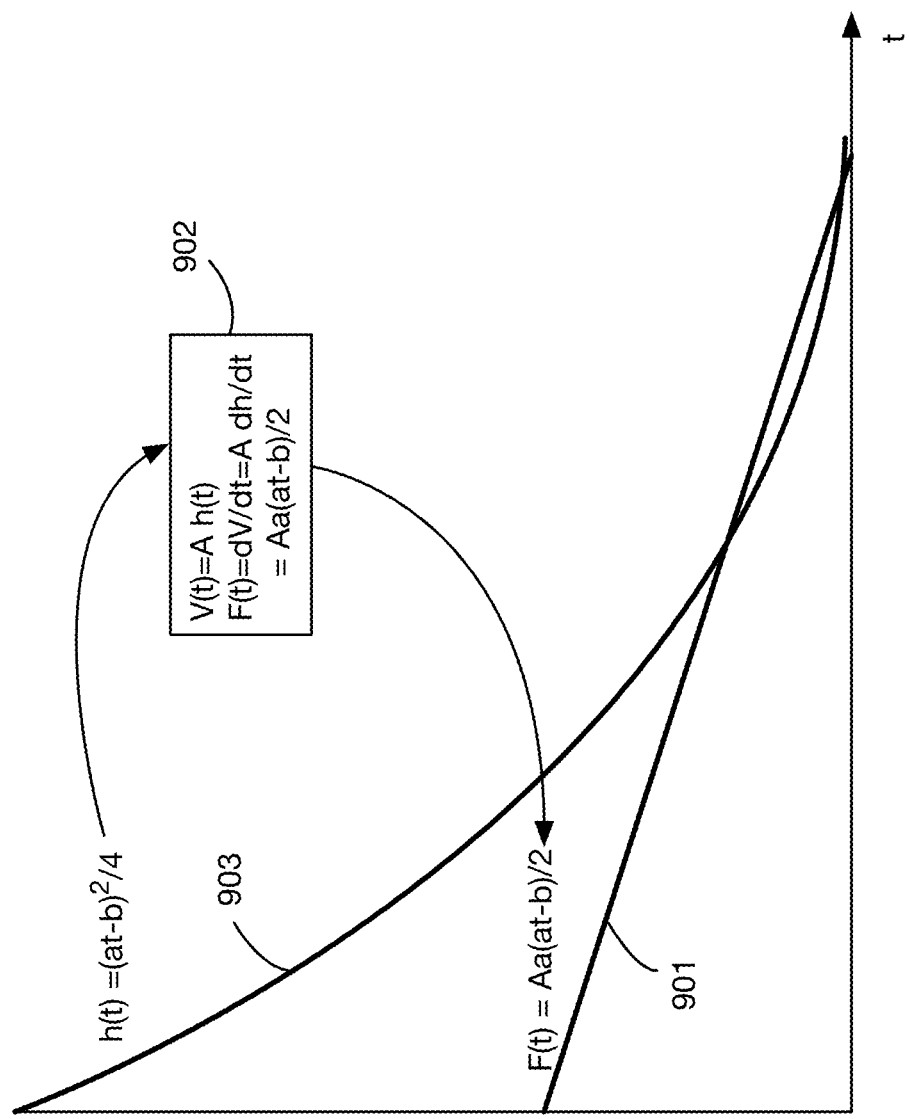
FIG. 9 shows an illustrative flow rate model that may be used in one or more embodiments to calculate flow metrics; in this model, flow rate increases as the height of the liquid in the container increases, due for example to higher pressure of the liquid on the filter.

FIG. 9 shows an illustrative flow rate model that may be used in one or more embodiments of the invention. The inventors have observed that empirically, in many filtering containers, after a hopper is filled with liquid, the flow rate 901 declines over time in an approximately linear relationship as the liquid in the hopper drains through the filter, and the height of the liquid 903 declines on a quadratic curve 903. For a container with constant cross-sectional area A, the flow rate 901 and height 903 will be related via equations 902, since the flow rate is the derivative of the volume in the hopper, and the volume is the cross-sectional area times the height. The quadratic height curve 903 may be parameterized for example by two parameters, a and b, which can be calculated from the capacitive sensor data, as described below.

FIG. 10 shows an example of calculation of the total volume of liquid added to the hopper (the "fill volume") using the flow rate model of FIG. 9. Because the hopper may not always be filled to the same height, the fill volume may be calculated in one or more embodiments from points in time on the capacitance curves. If the hopper is filled relatively quickly (compared to the time required to filter the hopper), the start of the filtering of liquid in the hopper may correspond closely to the time 622 when the liquid level passes the upper sensor 104b. (In other situations, corrections may be applied to compensate for filtering that may occur during filling.) The liquid reaches height 503b corresponding to the upper sensor 104b after a time period 1003b, and it reaches height 503a corresponding to the lower sensor 104a after a time period 1003a. Using the relationship 903 between liquid height and time, these two points 1004a and 1004b on curve 903 may be used to calculate parameters 1005, because they provide two equations in the two unknowns. The total fill height 1001 can then be calculated from these parameters, as well as the total fill volume 1006, and the average flow rate 1007.

Figure 11:
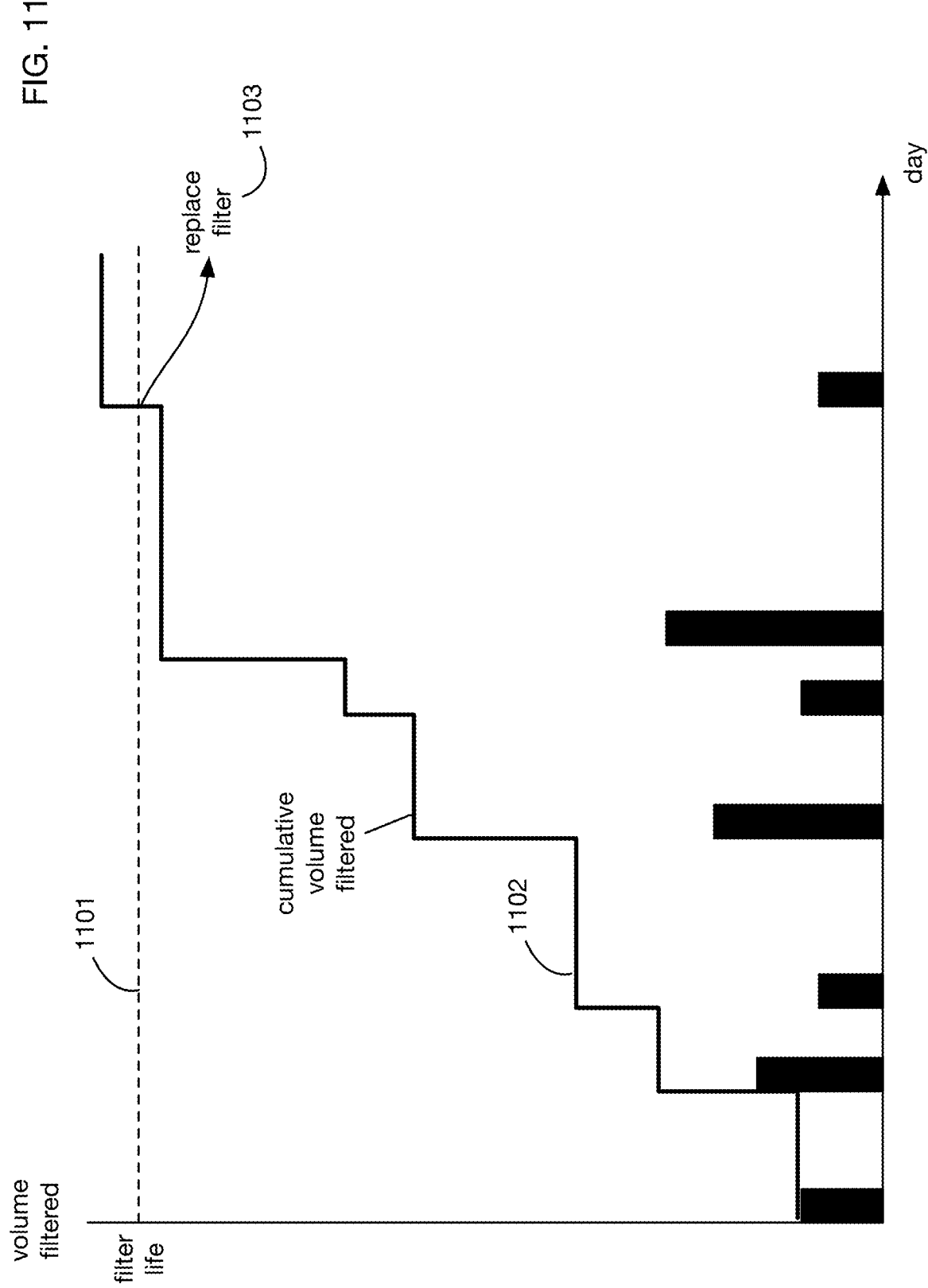
FIG. 11 illustrates calculation of the cumulative volume of liquid that passes through a filter, and use of this cumulative volume to signal when a filter should be replaced.

FIG. 11 shows how tracking of the fill volume into the hopper over a period of time may be used to determine when a filter needs to be replaced. Typically a filter may be rated to filter a specific cumulative amount of volume 1101 over its lifetime before being replaced. One or more embodiments of the invention may track the cumulative volume filtered to date 1102 through a filter by adding the fill volume to the running total each time the hopper is filled. This cumulative volume filtered 1102 may for example be tracked on a user's phone or in an internet database, or within the processor of the sensor package of the filtering container. A user may for example reset the cumulative volume filtered to zero when a new filter is installed, or in one or more embodiments a sensor in the container may detect when a new filter is installed, and may trigger a reset of the cumulative volume. When the cumulative volume filtered 1102 exceeds (or nears) the filter life 1101, a signal or message 1103 may be transmitted indicating that the filter should be replaced.

Figure 12:
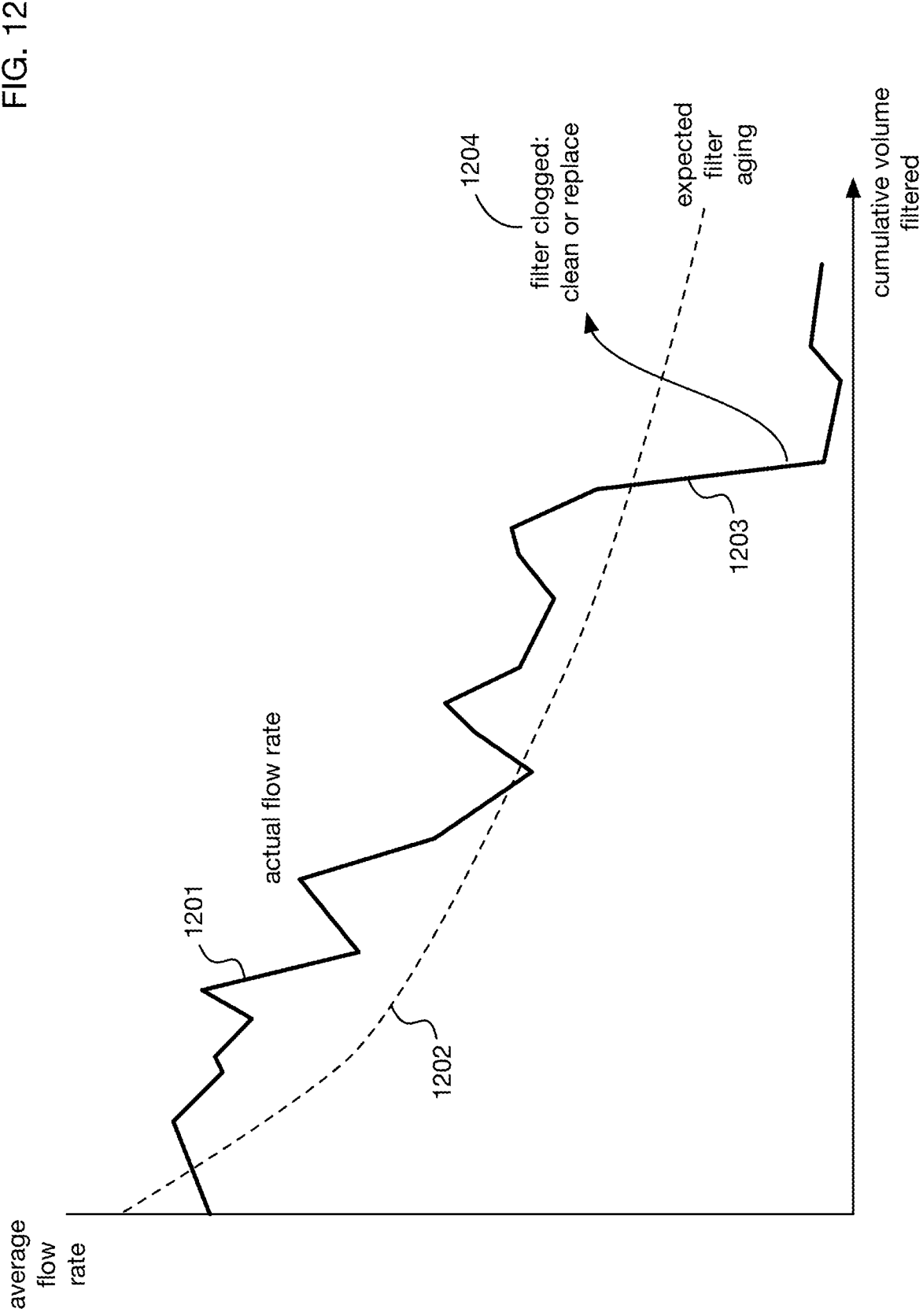
FIG. 12 illustrates tracking of changes in flow rate over time to determine when a filter may be clogged or may need to be replaced.

In addition to tracking cumulative volume filtered, one or more embodiments of the invention may track the filter flow rate over a period of time, as illustrated in FIG. 12. The measured flow rate 1201 may be compared to curve of the expected flow rate as a function of the cumulative volume filtered by a filter. Typically the flow rate will decrease as more volume is filtered through the filter. If this tracking shows a sudden discontinuity 1203 where the actual flow rate falls significantly below the expected value, a signal or message 1204 may be generated to suggest that the filter be cleaned or replaced.

Figure 13:
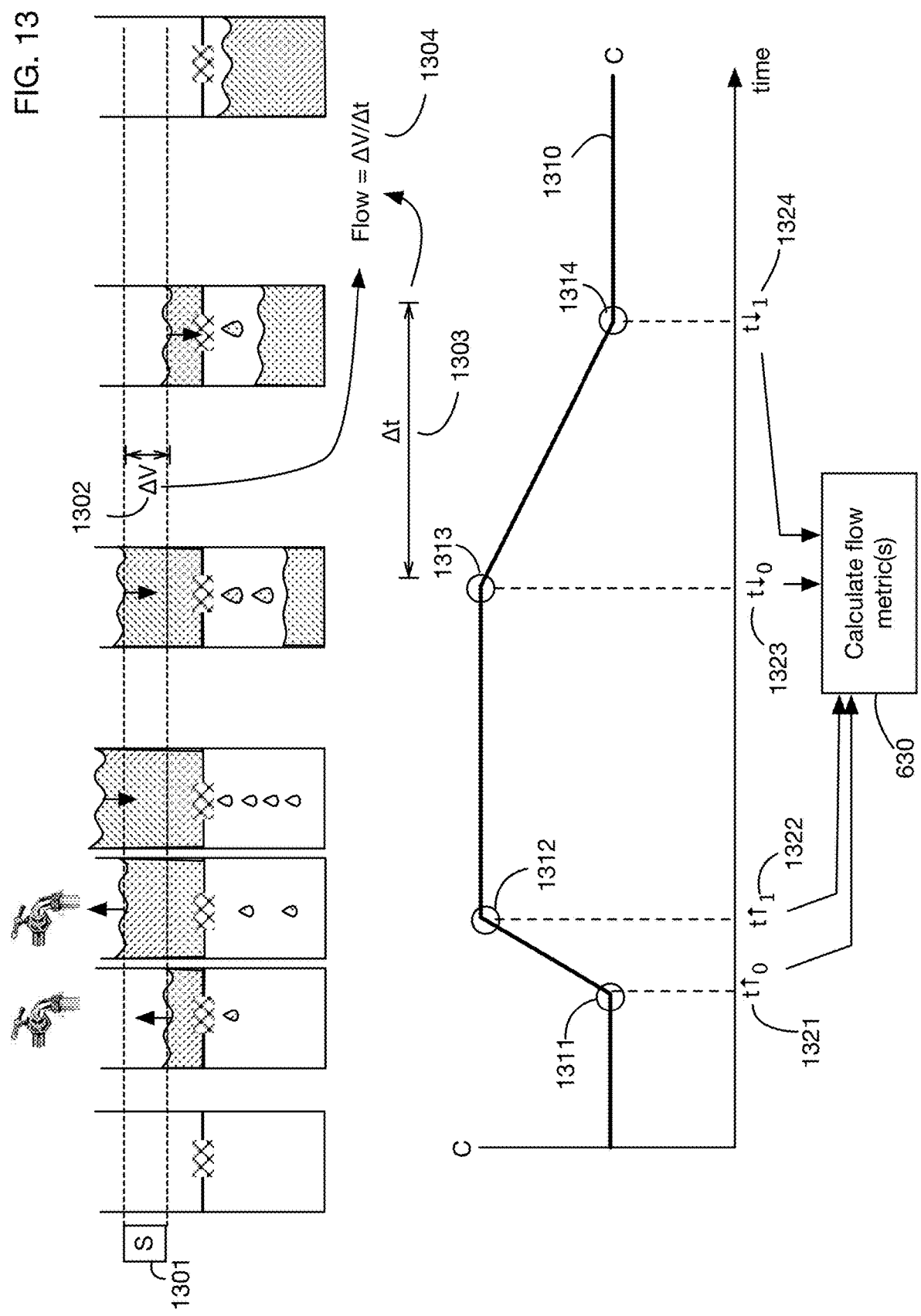
FIG. 13 shows a variation of the two-sensor strip embodiment of FIG. 5, which uses a single horizontal sensor strip and calculates flow metrics from points in time on the capacitance signal from this single strip.

Although the illustrative embodiments described above typically show two horizontal capacitive strips, one or more embodiments may use any number of strips; in particular, one or more embodiments may use only a single capacitive strip and may use the beginning and end points of the rising and falling edges of the capacitance curve as the points in time from which flow metrics are calculated. An embodiment with a single capacitive strip is illustrated in FIG. 13. The points in time 1321, 1322, 1323, and 1324 on the capacitance curve for sensor 1301 correspond respectively to the start of rising capacitance 1311, the end of rising capacitance 1312, the start of falling capacitance 1313, and the end of falling capacitance 1314. These points in time may be used to calculate flow metrics 630, as described above. In particular, an average flow rate 1304 may be calculated from the volume difference 1302 in the hopper between the liquid level at the top of sensor 1301 and the bottom of sensor 1301, and from the time difference 1303 between the time the liquid level passes the top edge of the sensor and the time it passes the bottom edge of the sensor. Similarly, an average hopper fill rate may be calculated from volume difference 1302 and the time difference between 1322 and 1321.

Figure 14:
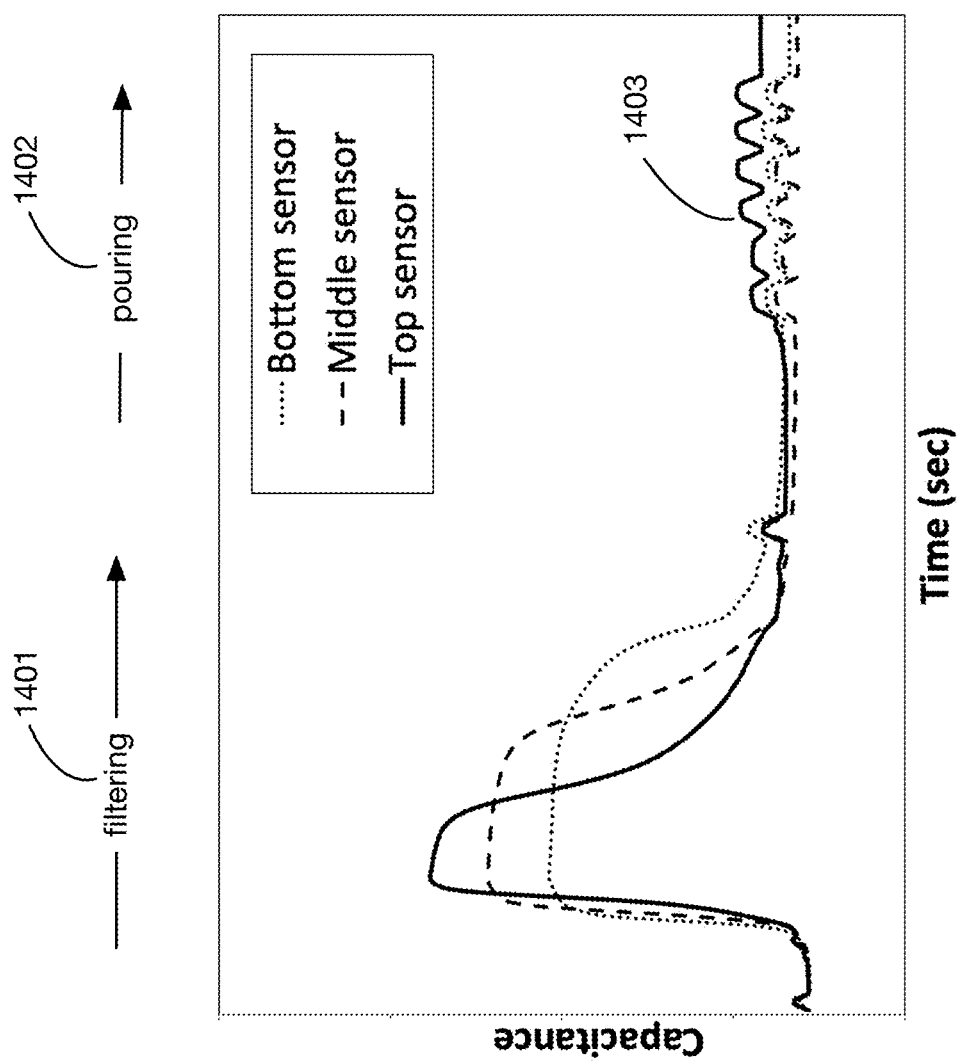
FIG. 14 shows capacitance signals when liquid is poured out of container after filtering, showing that the effect of this pouring is small.

In some situations, liquid in the hopper or reservoir of the filtering container may shift or slosh, due for example to movement of the container. This motion of the liquid may affect the capacitance of the capacitive sensor strips. One or more embodiments may process the capacitance signals, or combine capacitance data with other sensor data, to ensure that flow and filling metrics can be calculated even if the liquid in the container is in motion. Experiments by the inventors have shown that motion of the container when the liquid is in the reservoir, for example tilting the container to pour liquid out of it, has only a minor effect on measured capacitance if the sensors are not located near the reservoir's pour spout. (For this reason, in one or more embodiments the sensing package or "wand" containing the capacitive sensor strips may be physically located away from the pour spout.) FIG. 14 shows an illustrative experiment with three horizontal capacitive strips in a sensing package installed next to the hopper; liquid is added to a hopper and filtered in step 1401 into the reservoir, and then is poured in step 1402 out of the container. During pouring, the effect 1403 on capacitance signals is small, so that these capacitance changes can be easily differentiated from filling the hopper and filtering liquid through the filter. Alternately the different shapes of the capacitance vs time curves can be used to distinguish water filtering from pouring from the reservoir. In one or more embodiments, the system may have additional sensors (such as motion sensors or tilt sensors) that may be used to indicate when pouring is occurring, so that it can be distinguished from filtering.

Movement of the filtering container during filtering presents a more significant challenge, as illustrated for example in FIG. 15. In this experiment, a user held a container and walked with the container while liquid was filtered from the hopper. The resulting capacitance signals 1501 show significant noise due to the movement of the container. To compensate for this noise, one or more embodiments may for example apply a low-pass filter 1502 to the capacitance signals; this procedure is effective since the motion component of the signals are generally much higher frequency than the changes due to the fluid level rising and falling due to filling and filtering. The resulting filtered signals 1503 show the rising and falling edges clearly, allowing for calculation of flow metrics as described above. In various embodiments, the system may use software, numerical and/or hardware filtering.

Instead of or in addition to filtering the capacitance data, one or more embodiments may incorporate a baffle in the hopper to reduce movement of the liquid during filtering. The baffle may be for example a flexible (e.g., plastic) barrier to absorb energy and dampen the sloshing.

Figure 16B:
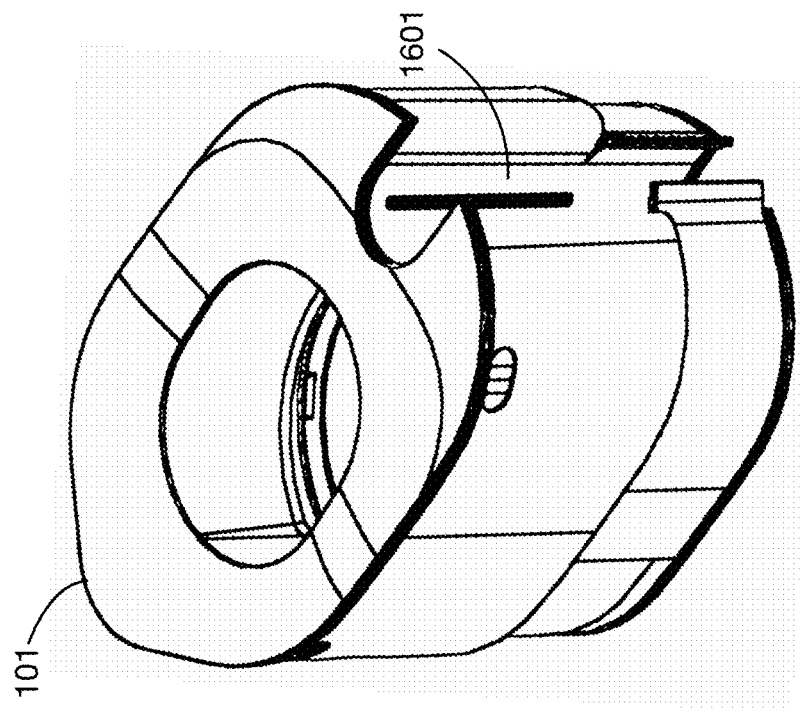
FIGS. 16A and 16B show top and perspective views, respectively, of an embodiment of a hopper with an indentation into which a sensing packaging can be inserted or removed for example for cleaning of the container.
Figure 16A:
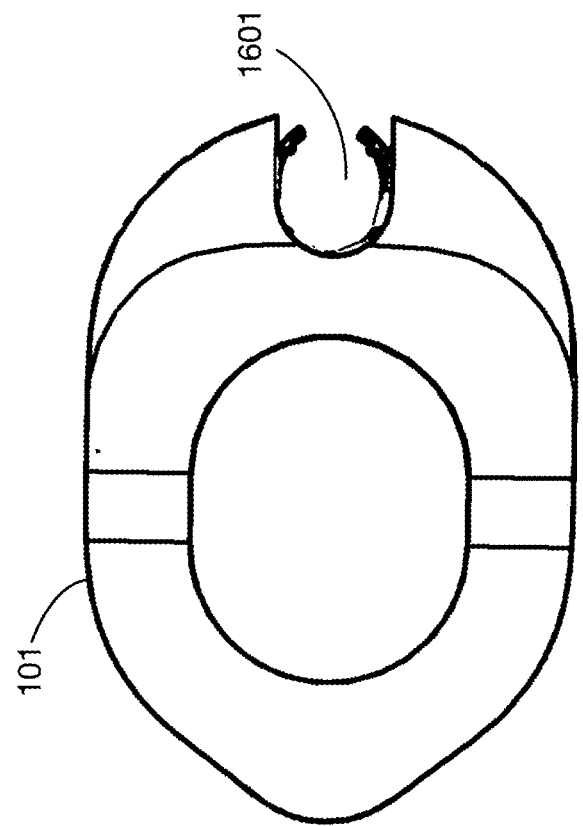

In one or more embodiments, the entire sensing package may be in a removable unit that can attach to the hopper for sensing, and detach from the hopper for example for cleaning of the container. FIGS. 16A and 16B show top and perspective views, respectively, of hopper 101 with the sensing package ("wand") 103 removed. (The handle of the hopper is also not shown for clarity). The walls of hopper 101 have an indentation 1601 into which the wand slides, and from which the wand can be easily removed. The indentation is on the side of the hopper opposite the pour spout, which may reduce the effect of pouring on the capacitance, as described above. This geometry for the hopper and wand is illustrative; one or more embodiments may attach a sensing package to any part of a hopper or other part of a container in any desired manner, using any desired shape and size for the hopper, container, and sensing package.

Figure 17:
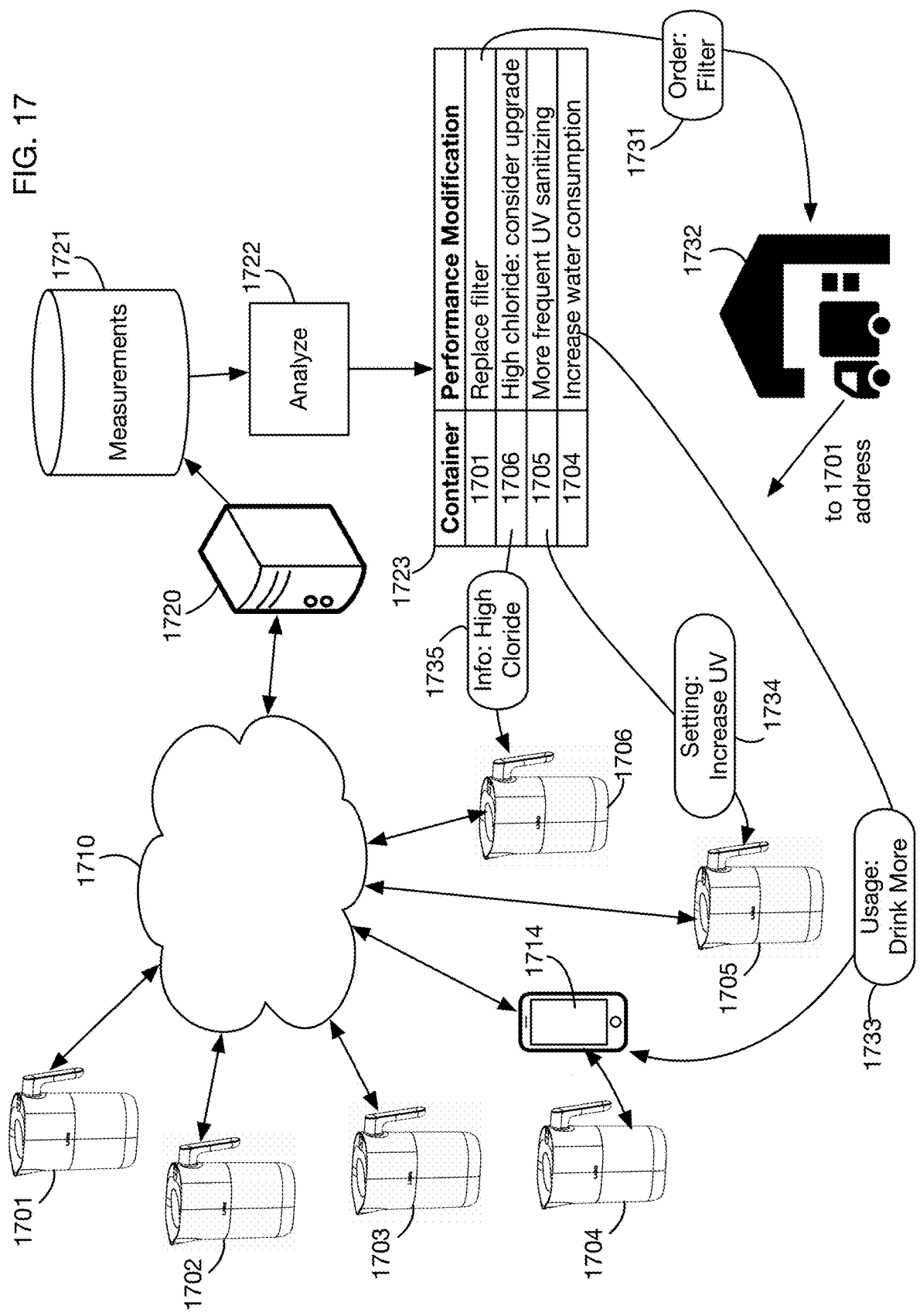
FIG. 17 shows an illustrative network of smart pitchers that upload data to a centralized database, and a processor that analyzes this data to generate performance improvement messages that are transmitted to the pitchers, to users, to fulfillment centers, or to other parties.

FIG. 17 shows an illustrative network of smart filtering containers. The illustrative containers shown are water pitchers; in one or more embodiments containers may be any type or types of vessels or devices that contain or process any type or types of liquids. FIG. 17 shows 6 illustrative containers 1701 through 1706; one or more embodiments may have any number of containers. In particular, in one or more embodiments the network and performance monitoring and management system may be connected to a very large number of containers, such as for example thousands or millions of containers. These containers may be geographically distributed over any region or area, including globally. Containers may be "smart" containers that may include embedded electronics, sensors, or actuators. Containers may be connected via a network or networks 1710 to a centralized processor or processors 1720. For example, without limitation, network 1710 may be the Internet, combined potentially with local gateways or relays to connect to containers, and processor 1720 may be one or more Internet-connected servers. Network connections between containers and the centralized processor or processors 1720 may use any type or types of links and protocols. For example, in one or more embodiments, some or all of the containers may be Internet-of-Things ("IoT") devices. The smart containers may have their own IP addresses and may communicate directly using Internet protocols (such as TCP/IP), or they may transmit data to routers, hubs, or gateways using other protocols such as Wi-Fi or Bluetooth. Containers may communicate with central processors via any number of links or intermediary devices or subnetworks. For example, in one or more embodiments, one or more containers may transmit data to a mobile device, which then forwards this data via an Internet connection to a central processor; this scenario is illustrated in FIG. 17 for pitcher 1704, which communicates locally with mobile phone 1714 (for example, over Bluetooth), and this mobile phone 1714 transmits data to or from an Internet connection.

In one or more embodiments, smart containers such as pitchers 1701 through 1706 may have sensors that generate sensor data, which may describe for example the usage of or status of the container or of the liquid in the container. This sensor data may be collected by a local controller within each smart container, and measurements based on the sensor data may be forwarded over network 1710 to the centralized processor or processors 1720. Processor 1720 may store some or all of these measurements in a database 1721. The local controllers within each container may transform sensor data into measurements in any desired manner, or raw sensor data may be transmitted directly as measurements. In one or more embodiments, additional processing, filtering, or analysis of measurements or data may be performed by intermediary devices such as mobile device 1714.

Central processor or processors 1720 may be any type of processing device or devices, including for example, without limitation, a computer, a desktop computer, a laptop computer, a notebook computer, a server, a tablet, a mobile device, a CPU, a GPU, or a network of any of these devices. Database 1721 may be any type of information store or stores, including for example, without limitation, relational databases, non-relational databases, or filesystems.

Processor 1720 may perform analyses 1722 of the measurements received from the containers. These analyses may for example scan the measurements for any types of patterns or correlations, or compare measurements to any desired criteria or thresholds. Centralized analysis of measurement data across an entire network of containers offers several potential benefits. First, the analyses 1722 may be performed on data from potentially very large numbers of containers. This allows the system to discover patterns and trends that would not be apparent from analysis of data from a single container. Second, substantial processing resources may be applied to data analysis that would not be possible or practical for local analysis of container data; for example, centralized processor 1720 may use specialized hardware such as GPUs to train machine learning models on the measurement database 1721. Third, results of analyses 1722 may be transmitted to multiple devices, organizations, or individuals; for example, as described below with respect to FIG. 19, correlated measurements from multiple containers that indicate possible water contamination in a specific region may be used to alert appropriate authorities.

Results of analyses 1722 may be used to generate messages that trigger actions or provide information. The analyses may indicate that one or more of the containers in the network may benefit from some type of change or performance modification; a performance modification may for example be any type of change in the container, its use, its environment, its configuration, or in the knowledge of the user of the container or any other party related to the user or the environment. In the illustrative example shown in FIG. 17, analyses 1722 of measurements 1721 indicate that performance modifications 1723 are desirable for four of the containers in the network, 1701, 1706, 1705, and 1704. For each of these containers, processor 1720 generates and transmits an associated message to effect or suggest the associated performance modification.

For example, analyses 1722 may indicate that the filter of container 1701 should be replaced. For example, the analyses may calculate the flow rate of liquid through the filter, and may determine that this flow rate is unusually low, which may suggest that the filter is clogged, slow, defective, or near the end of its expected life. Alternatively, analyses may calculate the total cumulative volume of liquid filtered through the filter, and determine that this cumulative volume is at or near the lifetime filtering capacity of the filter. The system may then send an order message 1731 to order a replacement filter. More generally the system may generate an order message to order any type of component, replacement, upgrade, test, refurbishing, instruction, kit, package, add-on, or item. Orders may be transmitted directly to a fulfillment center 1732, which may forward the ordered item or items directly to the site of the associated container. Alternatively the system may send a usage message to the user of a container recommending that the user place such an order, or it may send the order message to the user for confirmation.

For container 1706, analyses 1722 show high levels of chloride in the liquid filtered through the container; the system therefore generates an information message 1735 that informs the user of the container about this high level. The high chloride level may for example be detected by sensors in the associated container that analyze the liquid in the container, either before or after filtering. An information message may contain for example, without limitation, any analyses, measurements, suggestions, recommendations, ideas, conclusions, warnings, alerts, data, or instructions. Information messages may be transmitted to the users of the smart containers, or to any other party or parties. Information messages may for example provide information on any or all of the liquid, the filtered liquid, the user, and the container.

For container 1705, analyses 1722 indicate that the container would have improved performance if it performed sanitizing actions (for example using ultraviolet light) more frequently; a settings message 1734 is transmitted directly to the associated container 1705 to make this performance modifications. A settings message may modify any operational parameters of a smart container or of any other equipment related to the operation of the container. Settings messages may be transmitted directly to the container or equipment. In one or more embodiments, settings messages may be combined with information messages so that users are informed of the changes in settings.

For container 1704, analysis 1722 indicate that the user of the container is not consuming a recommended amount of water; the system therefore transmits a usage message 1733 to the user with a recommendation that the user increase his or her consumption. This message 1733 may for example be transmitted to mobile device 1714 of the user, or it may be transmitted to the container 1704 resulting in a display change on the container that indicates a need for more consumption. Usage messages may recommend any type of modification of the manner in which a filtering container or related equipment is used, including for example, without limitation, modifications of frequency of use, mode of use, type of liquid added, or configuration of the container.

The messages 1731, 1733, 1734, and 1735 shown in FIG. 17 are illustrative. In one or more embodiments, any type of message may be transmitted as a result of the analyses 1722 of measurements 1721. Messages may include for example, without limitation, order messages, information messages, settings messages, or usage messages. Messages may be transmitted to any person, device, or organization over any channel.

In one or more embodiments, local analysis of measurements or sensor data may be performed in addition to the analyses 1722 performed by the centralized processor 1720. For example, the electronics within each container may analyze sensor data directly, or a mobile device or other local processor such as phone 1714 may analyze data from the associated sensor and provide results and recommendations.

In one or more embodiments, containers such as 1701 through 1706 may be any types of devices or systems that hold, transport, or process any type of liquid. For example, without limitation, these containers may be water bottles, pitchers, hydration bladders, dispensers, fountains, filtering systems such as reverse osmosis systems for home water supplies, in-line filtration systems, or water treatment systems or facilities. These devices may store liquids, transport liquids, or process liquids. Processing of liquids may include any type of filtration or treatment. The devices may be for consumer use, industrial use, or both. Devices may be of any size or scale, ranging from small containers for personal use to entire water treatment facilities for communities.

Figure 18:
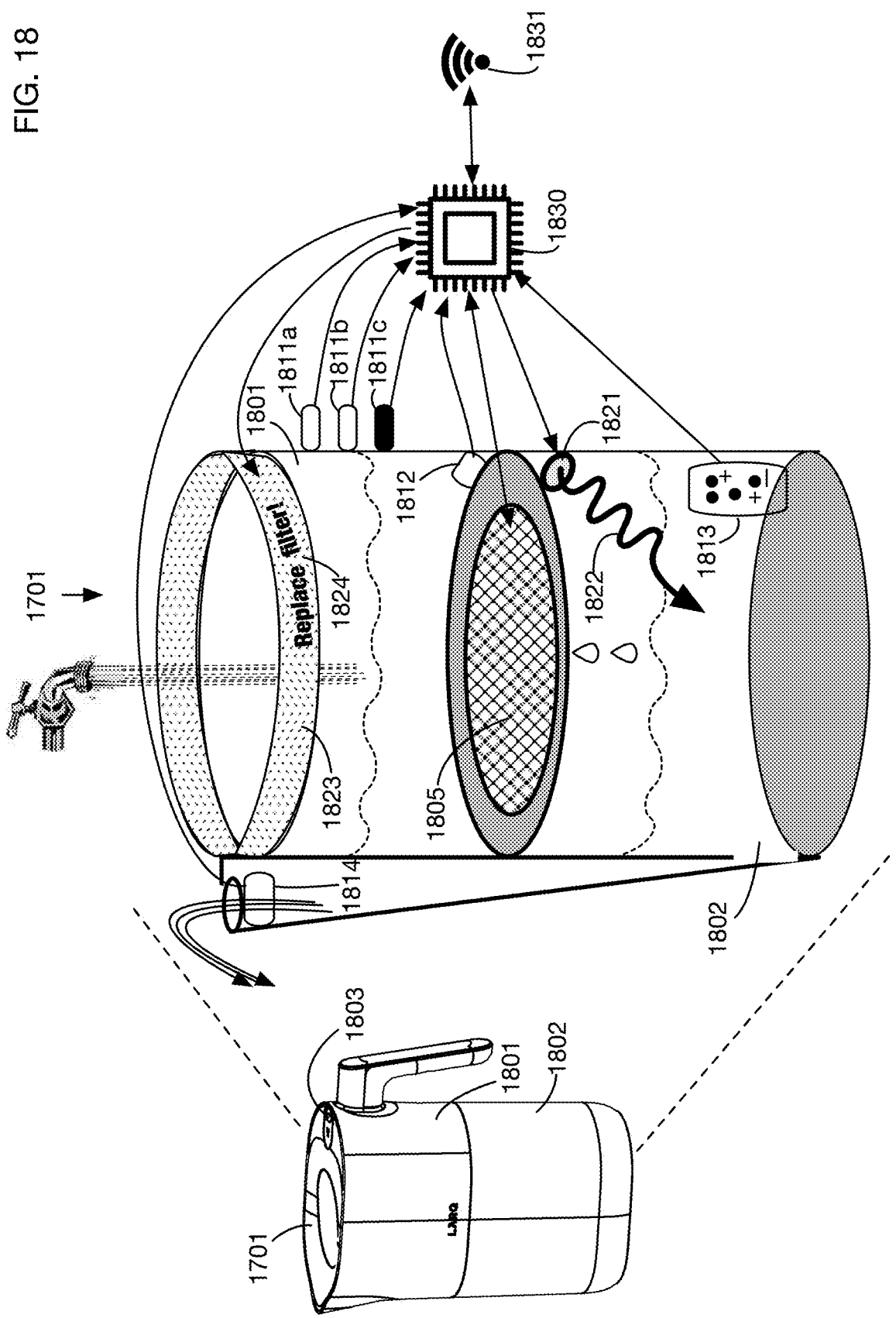
FIG. 18 shows an illustrative smart pitcher, which includes a filter, various sensors, and various actuators such as an ultraviolet light that sanitizes the liquid in the pitcher.

FIG. 18 shows an illustrative smart filtering container 1701 that may be used in one or more embodiments of the invention. One or more embodiments may connect to, monitor, and manage any type or types of containers for any type or types of liquids. These containers may be for example, without limitation, pitchers, bottles, dispensers, or jugs. The liquid contained in the containers may be water, or it may be other types of liquids including for example, without limitation, milk, soda, beer, wine, juice, or seltzer water.

Illustrative container 1701 is a pitcher with a hopper 1801 into which unfiltered liquid is placed, and a reservoir 1802 that contains filtered liquid. A filter may be between the hopper and the reservoir; the filter may remove one or more substance, such as impurities or contaminants, or otherwise treat the liquid in any desired manner as it passes from the hopper to the reservoir. Container 1701 may be smart container with electronics, sensors, or actuators, as described below with respect to the detailed view in FIG. 18.

In one or more embodiments, the electronics may be packaged in a removable module 1803 that mounts into or onto the container.

FIG. 18 shows a detailed view of illustrative components of container 1701. Embodiments may connect to and manage containers with any subsets of these components, or with additional or different components compared to those illustrated in FIG. 18. Container 1701 has a filter 1805 between hopper 1801 and reservoir 1802. Various sensors may be installed into the container. Each sensor may be electrically coupled to a controller 1830 that coordinates the transfer of data from the sensors. Controller 1830 may be any circuit or combination of circuits that manages the flow of data to or from one or more components of the container; for example, without limitation, controller 1830 may be a microprocessor, a microcontroller, a custom analog or digital circuit, an ASIC, or any combination thereof. Controller 1830 may also be coupled to one or more network interfaces 1831 for exchange of data with other devices or networks. The network interface(s) 1831 may be wired or wireless; wireless network interfaces may for example communicate via Bluetooth or Wi-Fi.

Illustrative container 1701 has liquid level sensors 1811*a*, 1811*b*, and 1811*c*. These sensors may be for example on or near the hopper 1801, and may measure the level of liquid in the hopper or changes in this level. These sensors may be for example capacitive sensor strips that change capacitance based on whether the region near the sensor contains liquid or air. The three sensors 1811*a*, 1811*b*, and 1811*c* are illustrative; one or more embodiments may have any number of liquid level sensors located in or near any part of the container.

Container 1701 also has a sensor 1812 that detects whether a filter 1805 is installed into the container. For example, this sensor 1812 may be switch that closes or opens based on whether a filter is currently (and correctly) installed.

Container 1701 has a liquid composition sensor 1813, which may for example be located within or near the reservoir, or in or near the hopper. This sensor may analyze the liquid to determine the presence or concentration of one or more substances in the unfiltered or filtered liquid, including but not limited to possible contaminants or harmful substances.

Container 1701 has a flow rate sensor 1814 located at or near the spout through which liquid is poured from the reservoir for consumption. In one or more embodiments, the flow of liquid from the container may be inferred for example from other measurements such as the liquid level sensors 1811*a*, 1811*b*, and 1811*c*.

Other sensors that may be present in one or more embodiments of the containers may include for example, without limitation, motion sensors, orientation sensors, temperature sensors, humidity sensors, light sensors, proximity sensors, or pressure sensors. Embodiments may use any type or types of sensors to collect any desired data that measures one or more characteristics of the liquid in the hopper, the filtered liquid in the reservoir, the filter, the hopper, the reservoir, any other component of the container, the configuration of the container or any of its components, the flow of liquid into the hopper, the flow of liquid through the filter, the flow of filtered liquid from the reservoir, or on changes in any of these factors.

Container 1701 may also be equipped with one or more actuators. These actuators may be coupled to and controlled by controller 1830. Container 1701 has an illustrative sanitizing actuator 1821 that sanitizes the liquid in the reservoir

1802. This actuator 1821 may be for example, without limitation, an ultraviolet light source that directs ultraviolet radiation towards the liquid in the reservoir, thereby inactivating bacteria and viruses. One or more embodiments may use other types of sanitizing actuators, such as heat, chemical treatment, aeration, agitation, or other forms of radiation. Sanitization may be directed at the liquid in the reservoir, the liquid in the hopper, or towards any portion or portions of the container itself such as the hopper, the reservoir, or the filter.

Container 1701 also has actuator 1823, which is an indicator light on the container. Controller 1830 may for example activate this indicator light to provide status information or instructions to the user of the container; as an example, the light may flash when it is time to replace the filter. In addition or alternatively, a display actuator panel or screen 1824 may be integrated into the container to display messages to the user. One or more embodiments may have other types of actuators to communicate with users, such as vibration actuators or speakers.

In one or more embodiments, filter 1805 may also have one or more elements that can be actuated or controlled to modify the functionality of the filter. For example, the filter may have settings that increase or decrease the selectivity with which certain materials are filtered out of the liquid.

Figure 19:
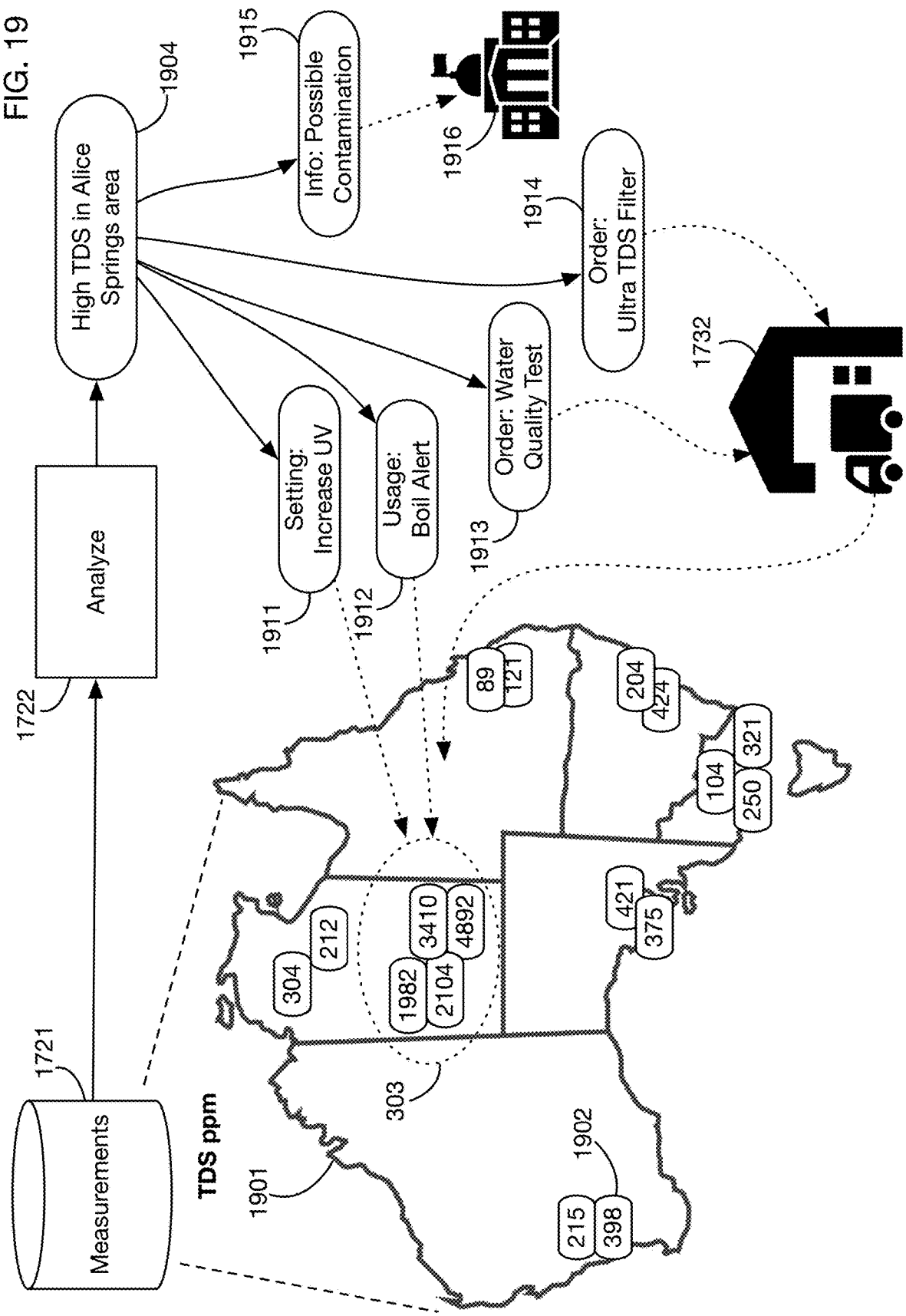
FIG. 19 shows an illustrative analysis of sensor data from a network of smart filtering containers; this analysis identifies regions where sensor measurements indicate possible contamination of local water or suggest particular filters or sanitizing actions.
Figure 20:
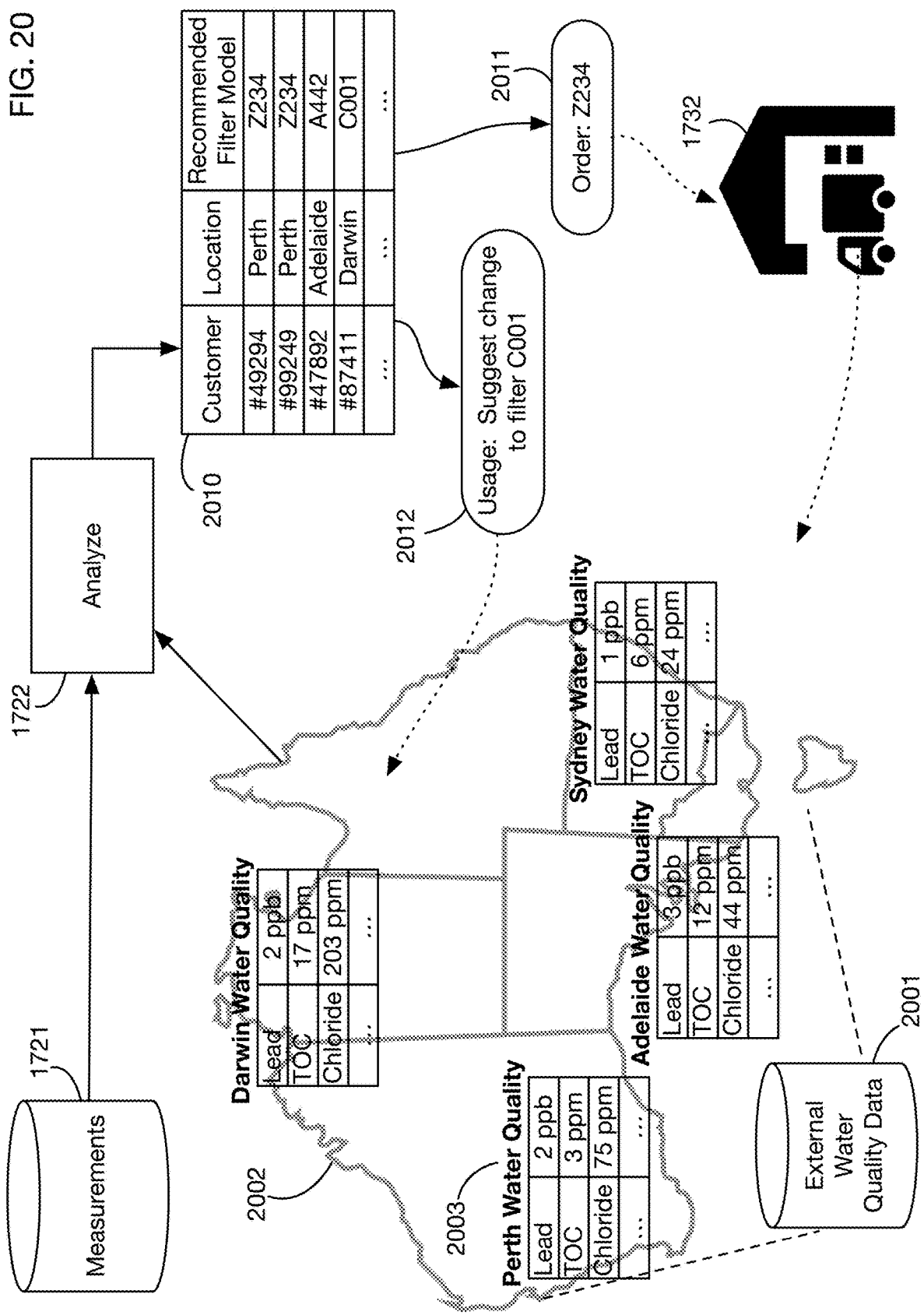
FIG. 20 shows a variation of the embodiment of FIG. 19, where the system obtains external water quality reports and uses this information to generate messages to pitchers, users, or fulfillment centers.
Figure 21:
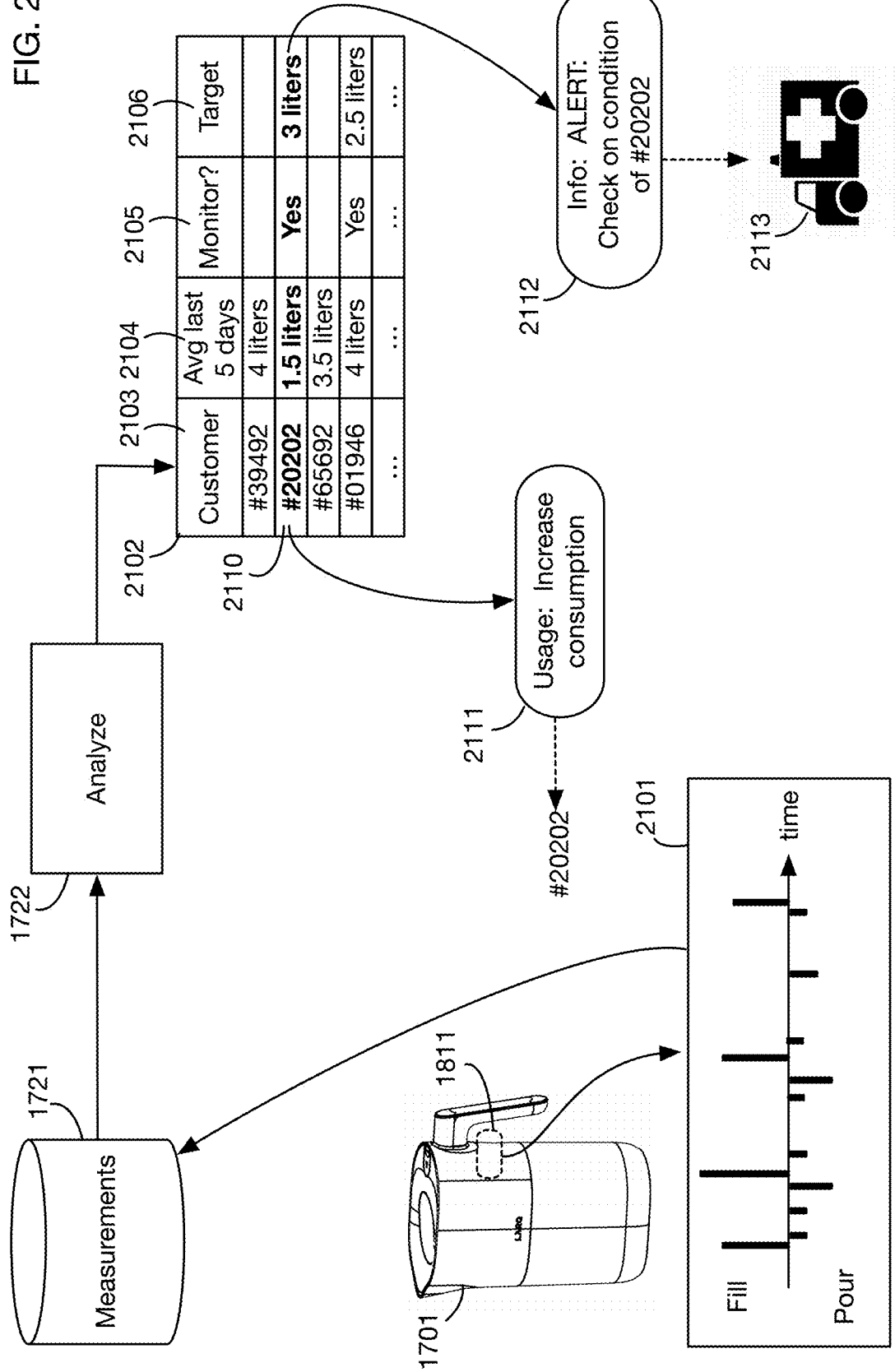
FIG. 21 shows an illustrative analysis of sensor data from pitchers that shows how much water is consumed by each user, and that identifies users that should be advised to drink more.

FIGS. 19 through 21 show illustrative analyses that may be performed by one or more embodiments on the measurements obtained from the network of smart filtering containers. FIG. 19 shows illustrative water quality measurements 1901 collected from a network of containers, for example from sensors such as sensor 1813 in FIG. 18. For example, sensor 1813 may measure the total dissolved solids ("TDS") in the water in the reservoir, which may be used as a measure of water quality. Each measurement such as measurement 1902 may be tagged in database 1721 with the location of the corresponding container. Analyses 1722 may therefore correlate measurements across sensors to look for geographical clusters of abnormal readings, which may for example indicate local water quality issues in specific regions. For example, cluster 1903 results in analysis 1904 because of the abnormally high TDS readings across a number of containers in that area. Triggered by this analysis result 1904, the system may generate one or more messages to respond to the identified cluster. For example, a settings message 1911 may be transmitted to the containers in that region to increase the level of sanitization, such as by increasing the duration or intensity of ultraviolet radiation, or modifying the schedule on which ultraviolet radiation occurs. A usage message 1912 may be sent to the users of containers in the affected area advising them for example to boil water temporarily or to seek other sources of water. An information message 1915 may be transmitted to local authorities 1916, such as agencies or organizations that monitor or influence water quality. An order message 1914 may be transmitted to fulfillment center 1732 to order specialized or upgraded filters for the containers in the affected area to compensate for the high TDS level. Another order message 1913 may be transmitted to a fulfillment center to order water quality tests that may assist in determining the specific composition of the TDS. These messages are illustrative; one or more embodiments may take any desired action and send any type or types of messages based on discovery of clusters or correlations across measurements.

One or more embodiments may compare and correlate measurements across containers in any desired manner, including but not limited to looking for geographic clusters of abnormal readings. For example, data mining on database 1721 may indicate correlations between container usage or performance and various factors such as user characteristics or environmental characteristics. These patterns may be used to develop targeted performance modification messages to the affected containers or users.

In one or more embodiments, external data sources may be used in addition to data from containers to determine whether performance modifications or messages are desired for one or more containers. FIG. 20 shows an illustrative example of a system that accesses external data 2001, which contains local water quality data for a number of zones within a geographical region 2002. This data may for example be generated be periodic water quality testing performed by local water agencies. Illustrative report 2003 shows for example the concentration of specific substances in the local water supply, such as lead, total organic carbon, and chloride for example. This data 2001 may be input into analyses 1722 along with measurements 1721 from the containers. Illustrative analysis 1722 may for example use the water quality data 2001 (potentially in addition to measurements from containers) to determine a recommended model or configuration of filter for each container. Filter recommendations may therefore be tailored to local water quality conditions. Recommendation results 2010 may be used for instance to transmit usage messages such as message 2012, which suggest to a user that a specific type of filter may be preferable, or to generate order messages such as message 2011 to directly order the appropriate filter for a particular user. Illustrative other external data sources that may be used for analyses 1722 may include for example, without limitation, weather history or forecast data, user demographic information, and purchase history data for related products and services.

FIG. 21 shows an illustrative embodiment that analyzes measurements 1721 from containers to determine the amount of water that a user is consuming over a period of time. For example, liquid level measurements 2101 from sensors 1811 in a container 1701 may be used to determine or estimate an average rate that liquid is being dispensed from that container. Analyses 1722 may generate a table 2102 of estimated consumption 2104 for each user 2103. In this embodiment, users may opt into or out of a monitoring service that monitors their consumption, and that alerts them (or others) when consumption may be inadequate. For example, column 2105 of table 2102 indicates whether a user is to be monitored, and column 2106 indicates the target consumption for that user. Illustrative user 2110 has opted into monitoring, and this user's consumption 2104 is below the target value 2106. As a result, the system may transmit a usage message 2111 to the user, advising the user to increase his or her consumption of water. In some situations an information message 2112 may also be sent to alert other parties, such as caregivers or medical personnel 2113, for example if the user requires assistance to maintain a healthy consumption of water.

Figure 22:
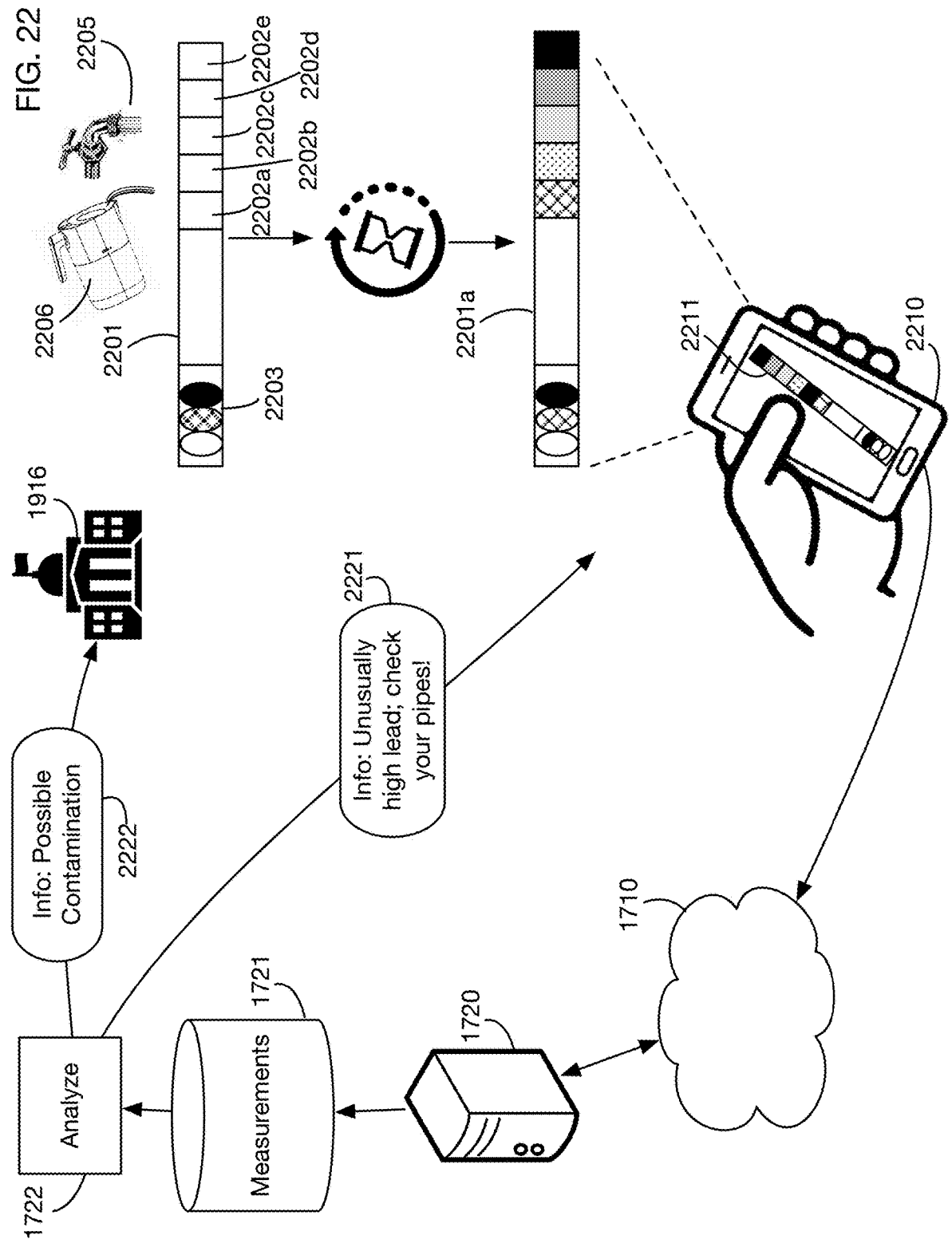
FIG. 22 shows an illustrative embodiment that includes an application to capture images of test strips that users can use to test their local water quality; test results or images may be sent to the central database for further analysis or actions.

One or more embodiments may enable water testing functionality to provide additional information that may be used to manage the network of smart filtering containers. FIG. 22 shows an illustrative example of an embodiment that allows users to perform tests of their water supply and to upload this data to the measurements database for analysis. For example, users may be provided with test strips or similar water testing materials 2201. Illustrative test strip 2201 may for example have a series of regions 2202a through 2202e that react with specific substances that may be present in the water supply; the regions may change colors or intensity depending on the presence of or concentration of the corresponding substances. The five regions 2202a through 2202e are for illustration; one or more embodiments may use test strips with any number of test regions. For example, one or more embodiments may use test strips with 15 test regions that test substances such as fluoride, total chlorine, total hardness, lead, iron, copper, pH, nitrite, nitrate, carbonate, bromine, cyanuric acid, total alkalinity, chloride, and ammonium.

The user may expose the test strip 2201 to either untreated water 2205 or filtered water 2206 dispensed from the filtering container. An image 2211 of the exposed test strip 2201a may then be captured by an application that executes for example on a mobile device 2210 or other device used by the user. The image, or information extracted from or based on the image, may then be uploaded over network 1710 to processor 1720, and stored in measurements database 1721. Analyses 1722 may then use the test results from individual users, in a manner similar to that illustrated in FIG. 20. For example, an information message 2222 may be sent to authorities 1916 if a user test indicates contamination, or an information message 2221 may be sent directly to the associated user. Filter recommendations may also be made based on the user's water quality test.

One challenge in interpreting the image 2211 of the test strip 2201a is that the colors or intensities of the regions 2202a through 2202e may be dependent on variable factors such as lighting, camera angles, camera quality, and user photographic technique. To compensate and control for these factors, in one or more embodiments the test strips 2201 may contain calibration areas 2203 with known colors or intensities. The appearance of these calibration areas in the image 2211 may then be used to adjust the image so that results are standardized.

While the invention herein disclosed has been described by means of specific embodiments and applications thereof, numerous modifications and variations could be made thereto by those skilled in the art without departing from the scope of the invention set forth in the claims.

What is claimed is:

1. A monitoring and performance management system for a network of smart filtering containers, comprising:
    a multiplicity of smart filtering containers, each smart filtering container of said multiplicity of smart filtering containers configured as a portable water pitcher comprising
        a hopper configured to receive a liquid;
        a filter coupled to said hopper and configured to remove one or more substances from said liquid to yield a filtered liquid;
        a reservoir coupled to said filter and configured to receive and store said filtered liquid;
        one or more sensors configured to measure one or more characteristics of one or more of
            said liquid,
            said filtered liquid,
            said filter,
            said hopper,
            said reservoir,
            a flow of said liquid into said hopper,
            a flow of said liquid through said filter,
            a flow of said filtered liquid from said reservoir;
        a network interface;
        a controller within said each smart filtering container coupled to said network interface and to each sensor of said one or more sensors, and wherein said controller of said each smart filtering container is configured to
            collect data from said one or more sensors, and
            transmit measurements based on said data from said one or more sensors via said network interface;
    wherein said multiplicity of smart filtering containers are geographically distributed over a region; and,
    a processor coupled via one or more network connections to said multiplicity of smart filtering containers, wherein said processor is external to said multiplicity of smart filtering containers, and wherein said processor is configured to
        receive said measurements based on said data from said one or more sensors from each of said multiplicity of smart filtering containers;
        analyze said measurements from each of said multiplicity of smart filtering containers to identify one or more smart filtering containers of said multiplicity of smart filtering containers for which a performance modification is desired; and,
        transmit a message associated with said one or more smart filtering containers of which said performance modification is desired, wherein said message comprises one or more of
            a settings message that sets or modifies an operational parameter of an associated smart filtering container of said one or more smart filtering containers,
            an order message that orders an item associated with said associated smart filtering container,
            a usage message that instructs a user of said associated smart filtering container to modify a usage of said associated smart filtering container,
            an information message that provides information related to one or more of said liquid, said filtered liquid, said user, and said associated smart filtering container.

2. The system of claim 1, wherein said analyze said measurements comprises calculate one or more of
    a flow rate through said filter; and,
    a cumulative volume of said liquid filtered through said filter.

3. The system of claim 2, wherein
said performance modification comprises replacement of said filter that is clogged, slow, defective, or at or near its expected life.

4. The system of claim 3, wherein
said order message comprises an order for a replacement filter for said associated smart filtering container.

5. The system of claim 3, wherein
said usage message comprises a recommendation to said user to replace said filter of said associated smart filtering container.

6. The system of claim 1, wherein
said analyze said measurements from said multiplicity of smart filtering containers comprises determine a water quality of one or both of said liquid and said filtered liquid.

7. The system of claim 6, wherein said information message further comprises additional information related to said water quality.

8. The system of claim 7, wherein said information message is transmitted to one or both of said user and an organization that monitors or influences said water quality.

9. The system of claim 6, wherein said order message further comprises an order for a water quality test or wherein said order message comprises an order for a replacement filter that is configured for said water quality.

10. The system of claim 6, wherein said processor is further configured to
correlate said water quality with locations of said multiplicity of smart filtering containers to determine said water quality in one or more regions.

11. The system of claim 1, wherein said processor is further configured to
obtain information on local water conditions for one or more regions in which said multiplicity of smart filtering containers are located; and,
transmit said information message based on said information on said local water conditions.

12. The system of claim 11, wherein said information message is transmitted to one or both of said user and an organization that is configured for said local water conditions.

13. The system of claim 11, wherein said order message comprises an order for a water quality test or a replacement filter that is configured for said local water conditions.

14. The system of claim 1, wherein
each smart filtering container of said multiplicity of smart filtering containers further comprises
a sanitization actuator, wherein said sanitization actuator of each smart filtering container is coupled to and controlled by said controller, and wherein said sanitization actuator is configured to sanitize one or more
of said liquid;
said filtered liquid;
said hopper;
said reservoir; and
said filter.

15. The system of claim 14, wherein said sanitization actuator comprises an ultraviolet light that is configured to emit ultraviolet radiation.

16. The system of claim 15, wherein said settings message modifies one or more of a duration, schedule, or intensity of said ultraviolet radiation.

17. The system of claim 15, wherein said usage message comprises a recommendation to said user to modify one or more of a duration, schedule, or intensity of said ultraviolet radiation.

18. The system of claim 14, wherein said processor is further configured to
obtain information on local water conditions for one or more regions in which said multiplicity of smart filtering containers are located; and,
transmit said message to one or more of said multiplicity of smart filtering containers in said one or more regions based on said local water conditions.

19. The system of claim 1, wherein said analyze said measurements from said multiplicity of smart filtering containers comprises
estimate an amount of said liquid dispensed over a time period from one or more of said multiplicity of smart filtering containers.

20. The system of claim 19, wherein
said one or more smart filtering containers of said multiplicity of smart filtering containers for which said performance modification is desired comprises said one or more smart filtering containers for which said amount of said liquid dispensed over said time period is below a threshold value; and,
said usage message comprises a recommendation to increase liquid consumption.

21. The system of claim 20, wherein said processor is further configured to
transmit said information message to a person or organization associated with said user, wherein said information message comprises an alert that said user is not consuming sufficient liquid.

22. The system of claim 1, further comprising
a testing application configured to execute on a device used by said user, wherein said testing application is configured to
capture an image of a test that said user has exposed to one or both of said liquid and said filtered liquid, wherein said test is configured to change an appearance based on said one or more substances that may be present in said liquid or said filtered liquid;
transmit image information based on said image to said processor;
wherein said processor is further configured to
analyze said image information from said multiplicity of smart filtering containers to determine a water quality of one or both of said liquid and said filtered liquid.

23. The system of claim 22, wherein said test comprises
a test region configured to change said appearance based on said one or more substances that may be present in said liquid or said filtered liquid; and,
one or more reference regions comprising reference colors.

24. The system of claim 22, wherein said information message comprises information related to said water quality.

25. The system of claim 24, wherein said information message is transmitted to one or both of said user and an organization that monitors or influences said water quality.

26. The system of claim 22, wherein said order message comprises an order for a replacement filter that is configured for said water quality.

27. The system of claim 22, wherein said processor is further configured to
correlate said water quality with locations of said multiplicity of smart filtering containers to determine said water quality in one or more regions.

28. The system of claim 1,
wherein said hopper comprises
an inside wall in contact with said liquid, and
an outside wall not in contact with said liquid; and,
wherein said one or more sensors of at least one of said multiplicity of smart filtering containers comprises
one or more horizontal capacitive sensor strips proximal to said hopper and not in contact with said liquid and not in contact with said inside wall of said hopper, wherein
said one or more horizontal capacitive sensor strips do not extend vertically across a full height of said liquid in said hopper when said hopper is filled with said liquid; and,
wherein said controller or said processor is configured to
receive capacitance data from each of said one or more horizontal capacitive sensor strips;
identify points in time in said capacitance data from said each of said one or more horizontal capacitive sensor strips, wherein each point in time of said points in time corresponds to an associated height of said liquid in said hopper;
calculate one or more flow metrics from said points in time.

29. The system of claim 1, wherein said each smart filtering container further comprises an Internet Protocol (IP) address such that said each smart filtering container of said multiplicity of smart filtering containers are further configured to communicate directly using said IP address.

30. The system of claim 1, wherein said analyze said measurements comprises scanning said measurements to detect patterns or correlations or trends across said multiplicity of smart filtering containers.

* * * * *